US012295852B2

(12) United States Patent
Robicheaux et al.

(10) Patent No.: US 12,295,852 B2
(45) Date of Patent: May 13, 2025

(54) CANAL SPARING HUMERAL IMPLANT AND RELATED METHODS

(71) Applicant: Encore Medical, LP, Austin, TX (US)

(72) Inventors: Alysha Robicheaux, Austin, TX (US); Ellen Chen, Austin, TX (US)

(73) Assignee: Encore Medical, LP, Austin, TX (US)

( * ) Notice: Subject to any disclaimer, the term of this patent is extended or adjusted under 35 U.S.C. 154(b) by 120 days.

(21) Appl. No.: 17/351,500

(22) Filed: Jun. 18, 2021

(65) Prior Publication Data
US 2021/0393414 A1 Dec. 23, 2021

Related U.S. Application Data

(60) Provisional application No. 63/184,345, filed on May 5, 2021, provisional application No. 63/040,796, filed on Jun. 18, 2020.

(51) Int. Cl.
*A61F 2/40* (2006.01)
*A61F 2/30* (2006.01)

(52) U.S. Cl.
CPC ........ *A61F 2/4014* (2013.01); *A61F 2/30771* (2013.01); *A61F 2/4003* (2013.01); *A61F 2002/30011* (2013.01); *A61F 2002/30616* (2013.01); *A61F 2002/30845* (2013.01); *A61F 2002/30884* (2013.01); *A61F 2002/30904* (2013.01); *A61F 2002/4018* (2013.01); *A61F 2002/4033* (2013.01)

(58) Field of Classification Search
CPC .................. A61F 2/3601; A61F 2/4003; A61F 2002/3603; A61F 2002/4007
See application file for complete search history.

(56) References Cited

U.S. PATENT DOCUMENTS

| 4,042,980 | A | 8/1977 | Swanson et al. |
| 4,550,450 | A | 11/1985 | Kinnett |
| 6,783,549 | B1 | 8/2004 | Stone et al. |
| 7,445,638 | B2 * | 11/2008 | Beguin ................. A61F 2/4014 623/19.12 |

(Continued)

FOREIGN PATENT DOCUMENTS

EP 2663263 B1 5/2014

OTHER PUBLICATIONS

Arthrex Gmbh, "Arthrex ECLIPSE (TM)—Stemless Shoulder Prosthesis Surgical Technique," Jan. 2017, pp. 1-13.

(Continued)

*Primary Examiner* — Megan Y Wolf
(74) *Attorney, Agent, or Firm* — Veros Legal Solutions, LLP

(57) ABSTRACT

A humeral implant is provided. The implant includes a humeral stem including a plurality of fins. At least one fin comprises a serrated bottom edge. A radial distance between an inner bottom edge of the at least one fin and a centerline of the humeral implant increases along a distal length of extension of the at least one fin. At least the serrated bottom edge of the at least one fin is configured to cut into and compact bone of the metaphysis of a humerus toward relatively denser cancellous bone of a peripheral portion of the humerus when press-fit therein, thereby providing sufficient press-fitting for cementless fixation of the humeral stem into the humerus. Related kits and methods are also provided.

18 Claims, 38 Drawing Sheets

(56) References Cited

U.S. PATENT DOCUMENTS

| | | | |
|---|---|---|---|
| 8,317,871 B2 | 11/2012 | Stone et al. | |
| 8,506,638 B2 | 8/2013 | Vanasse et al. | |
| 8,753,402 B2 | 6/2014 | Winslow et al. | |
| 8,876,908 B2 | 11/2014 | Katrana et al. | |
| 9,326,865 B2 | 5/2016 | Katrana et al. | |
| 9,820,859 B2 | 11/2017 | Gervasi et al. | |
| 2001/0047210 A1 | 11/2001 | Wolf | |
| 2009/0187247 A1* | 7/2009 | Metcalf, Jr. | A61F 2/447 606/301 |
| 2010/0114326 A1 | 5/2010 | Winslow et al. | |
| 2014/0107792 A1* | 4/2014 | Hopkins | A61F 2/4003 623/19.14 |
| 2014/0188244 A1 | 7/2014 | Thomas et al. | |
| 2016/0262903 A1* | 9/2016 | West | A61F 2/4202 |
| 2017/0105843 A1* | 4/2017 | Britton | A61F 2/4081 |
| 2021/0007856 A1* | 1/2021 | Nelson | A61F 2/30749 |
| 2021/0307918 A1* | 10/2021 | Deransart | A61F 2/30749 |
| 2021/0346166 A1* | 11/2021 | Sapio | A61F 2/30767 |

OTHER PUBLICATIONS

International Preliminary Report on Patentability received for WO Patent Application Serial No. PCT/US2021/38045 dated Dec. 29, 2022, 12 pages.

\* cited by examiner

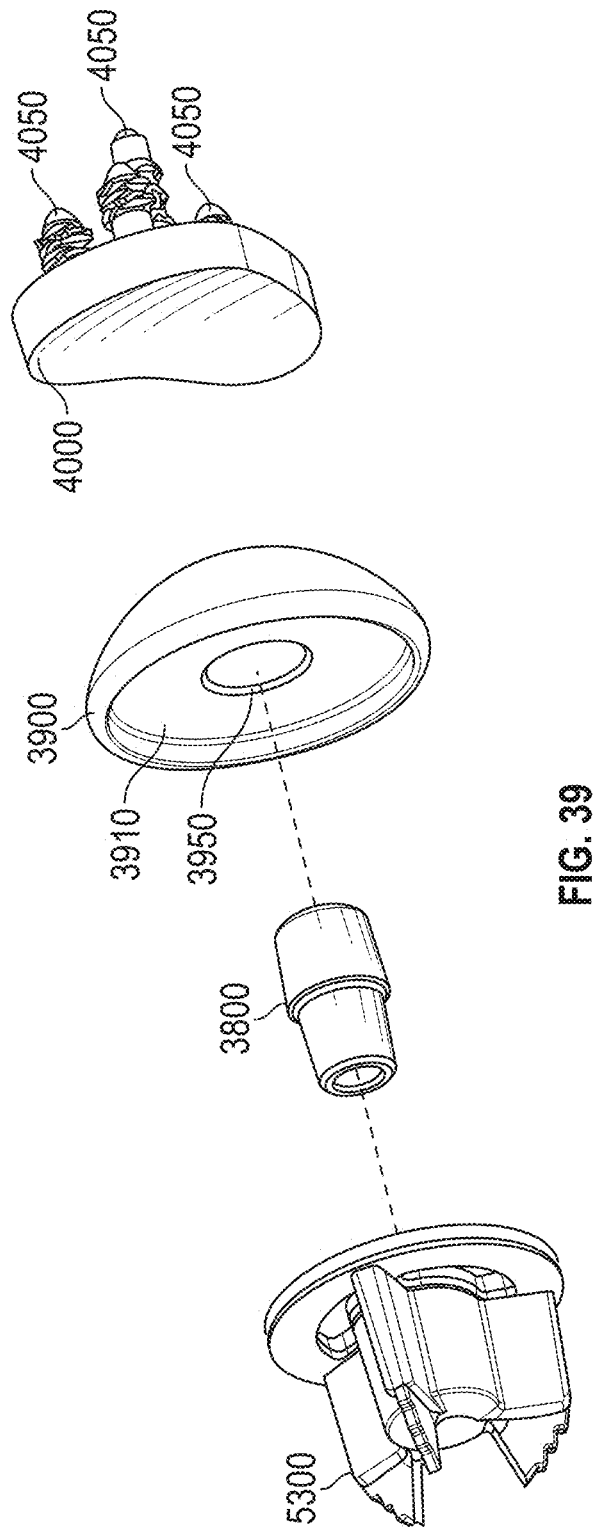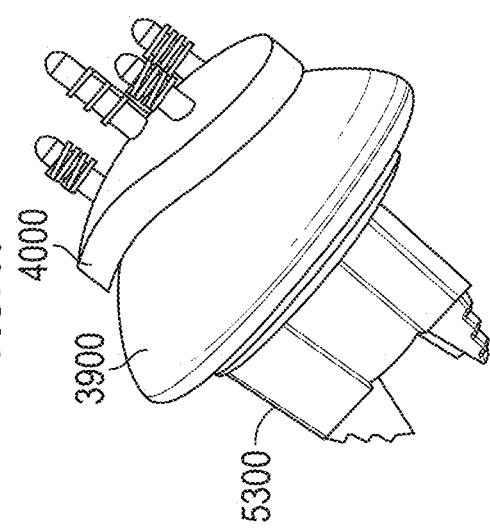
FIG. 39
FIG. 40

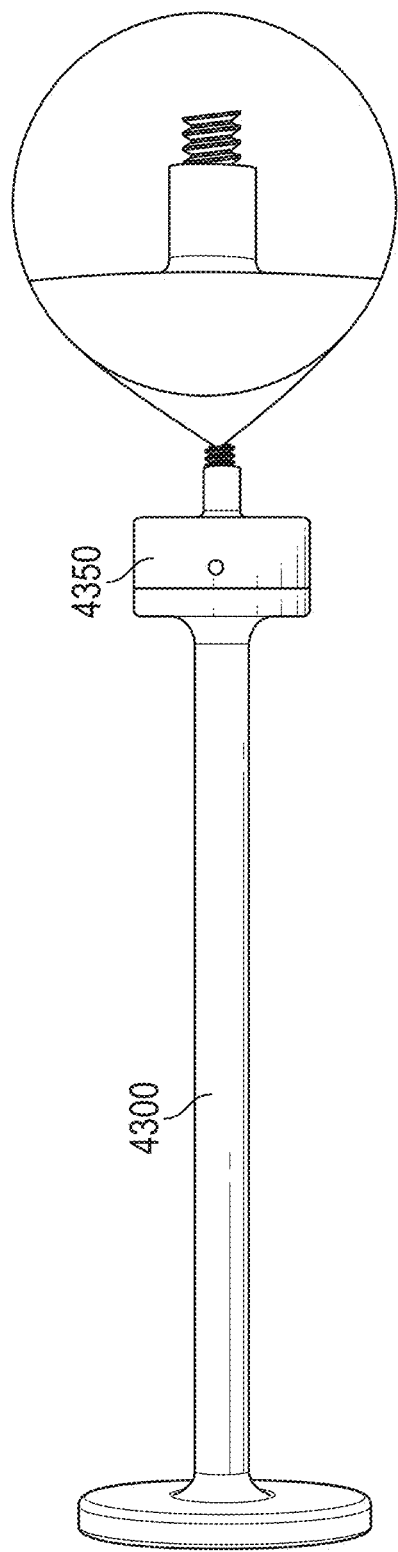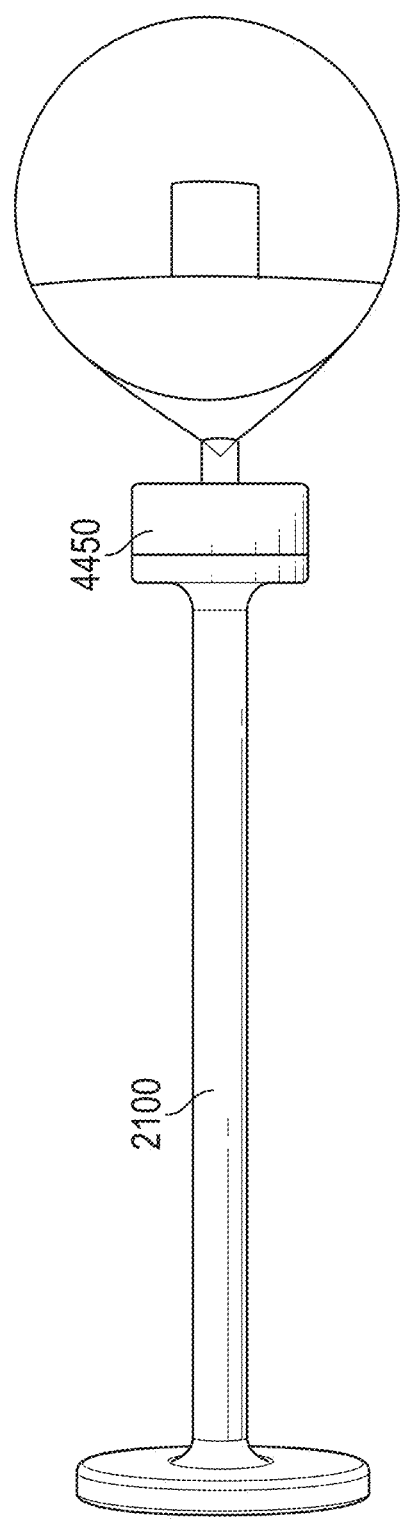
FIG. 43
FIG. 44

CANAL SPARING HUMERAL IMPLANT AND RELATED METHODS

CROSS-REFERENCE TO RELATED APPLICATIONS

This application claims the benefit of the filing date of U.S. Provisional Patent Application No. 63/040,796, filed on Jun. 18, 2020, and entitled "Canal Sparing Humeral Implant," and the benefit of the filing date of U.S. Provisional Patent Application No. 63/184,345, filed on May 5, 2021, and entitled "Canal Sparing Humeral Implant and Related Methods," the disclosures of which are hereby incorporated by reference herein in their entirety.

BACKGROUND

The present disclosure relates to implants, systems and/or kits for shoulder arthroplasty and associated methods.

Shoulder arthroplasty is a surgical procedure, often utilized to treat and/or alleviate chronic pain in arthritic and/or otherwise damaged shoulders, in which a portion of one or both of a humerus and its socket are replaced with implanted components designed to restore some or all of the natural range of motion and stability in the affected shoulder joint. However, implantation (and in some cases revision) of implants can require extensive remodeling and/or alteration of the bones and soft tissues involved, especially the humerus of the upper arm. Accordingly, a need exists for implants, systems and/or kits for shoulder arthroplasty, and associated methods, that allow for sparing of bone while also providing the ability for easy revision surgery.

SUMMARY

In some embodiments, a humeral implant is provided. The humeral implant includes a humeral stem comprising a plurality of fins, wherein at least one fin comprises a serrated bottom edge.

In some embodiments, each of the plurality of fins comprises a serrated bottom edge. In some embodiments, a radial distance between a medial edge of the at least one fin and a centerline of the humeral implant increases along a distal length of extension of the at least one fin. In some embodiments, at least the serrated bottom edge of the at least one fin is configured to cut into and compact bone of a medial portion of the metaphysis of a humerus toward relatively denser cancellous bone of a peripheral portion of the humerus when press-fit therein, thereby providing sufficient press-fitting for cementless fixation of the humeral stem into the humerus. In some embodiments, the humeral implant includes a central body and the plurality of fins extend radially away from the central body. In some embodiments, the central body has a substantially cylindrical shape that tapers slightly along its length of extension. In some embodiments, at least a portion of the plurality of fins extends farther distally than central body, thereby allowing for metaphyseal placement of the humeral implant in a humerus of a patient that avoids the humeral canal morphology. the plurality of fins are equally spaced about the central body. In some embodiments, the humeral implant includes a collar, wherein the collar comprises a plurality of windows and a porous coating configured to promote bone ingrowth of the humerus onto the collar. In some embodiments, the collar comprises an outer ring and a central portion and the plurality of windows, together, have a substantially circular shape interrupted by portions of the collar coupling the outer ring and the central portion, the collar has a substantially circular shape. In some embodiments, the humeral stem further comprises a porous coating on the at least one fin. In some embodiments, the porous coating comprises pores of varying sizes, thereby aiding in apposition of bone ingrowth. In some embodiments, implanting of the humeral implant simultaneously and artificially increases a density of the bone surrounding the humeral implant.

In some other embodiments, a method of implanting a humeral implant in a humerus of a patient is provided. The method includes performing an osteotomy cut of the head of the humerus along a humeral head resection plane. The method includes reaming out an inner portion of the humerus below the humeral head resection plane. The method includes press-fitting a humeral stem into the reamed inner portion of the humerus, the stem comprising a plurality of fins, wherein at least one fin comprises a serrated bottom edge.

In some embodiments, each of the plurality of fins comprises a serrated bottom edge. In some embodiments, a radial distance between a medial edge of the at least one fin and a centerline of the humeral implant increases along a distal length of extension of the at least one fin. In some embodiments, at least the serrated bottom edge of the at least one fin is configured to cut into and compact bone of a medial portion of the metaphysis of a humerus toward relatively denser cancellous bone of a peripheral portion of the humerus when press-fit therein, thereby providing sufficient press-fitting for cementless fixation of the humeral stem into the humerus. In some embodiments, the humeral stem further comprises a central body, wherein the plurality of fins extend radially away from the central body. In some embodiments, the central body has a substantially cylindrical shape that tapers slightly along its length of extension. In some embodiments, at least a portion of the plurality of fins extends farther distally than central body, thereby allowing for metaphyseal placement of the humeral stem in a humerus of a patient that avoids the humeral canal morphology. In some embodiments, the plurality of fins are equally spaced about the central body. In some embodiments, the humeral stem further comprises a collar comprising a plurality of windows and a porous coating configured to promote bone ingrowth of the humerus onto the collar. In some embodiments, the collar comprises an outer ring and a central portion and the plurality of windows, together, have a substantially circular shape interrupted by portions of the collar coupling the outer ring and the central portion. In some embodiments, the collar has a substantially circular shape. In some embodiments, the humeral stem further comprises a porous coating on the at least one fin. In some embodiments, the porous coating comprises pores of varying sizes, thereby aiding in apposition of bone ingrowth. In some embodiments, implanting of the humeral stem simultaneously and artificially increases a density of the bone surrounding the humeral stem. In some embodiments, the method includes disposing a shaft of a pin guide through an aperture of a humeral head trial such that a body of the pin guide, from which the shaft extends, is disposed within a recess in a bottom surface of the humeral head trial and the shaft extends away from a convex top surface of the humeral head trial, centering the coupled humeral head trial and pin guide on the osteotomy cut, disposing a guide pin through a cannula in the shaft of the pin guide and securing the guide pin into the head of the humerus, and removing the coupled humeral head trial and pin guide over the secured guide pin. In some embodiments, the method includes before press-fitting the humeral stem into the reamed inner portion of the humerus, performing one or both of: (1) disposing a canulated core drill onto the secured guide pin, drilling out a core of the reamed inner portion of the humerus utilizing the cannulated core drill while disposed on the secured guide pin, and removing the cannulated core drill over the secured guide pin, and/or (2) securing a cannulated punch to a cannulated punch handle, disposing the secured punch and punch handle onto the secured guide pin, impacting the punch handle until the punch is sufficiently impacted within the reamed inner portion of the humerus, detaching the punch handle from the impacted punch and removing the punch handle over the secured guide pin.

In some other embodiments, a method of manufacturing a humeral implant is provided. The method includes forming a humeral stem comprising a plurality of fins, wherein at least one fin comprises a serrated bottom edge.

In some embodiments, each of the plurality of fins comprises a serrated bottom edge. In some embodiments, a radial distance between a medial edge of the at least one fin and a centerline of the humeral implant increases along a distal length of extension of the at least one fin. In some embodiments, the at least one fin is configured to cut into and compact bone of a medial portion of the metaphysis of a humerus toward relatively denser cancellous bone of a peripheral portion of the humerus when press-fit therein, thereby providing sufficient press-fitting for cementless fixation of the humeral stem into the humerus. In some embodiments, the method includes forming the humeral stem to have a central body such that the plurality of fins extend radially away from the central body. In some embodiments, the method includes forming the central body to have a substantially cylindrical shape that tapers slightly along its length of extension. In some embodiments, at least a portion of the plurality of fins extends farther distally than central body, thereby allowing for metaphyseal placement of the humeral implant in a humerus of a patient that avoids the humeral canal morphology. In some embodiments, the plurality of fins are equally spaced about the central body. In some embodiments, the method includes forming the humeral stem to have a collar comprising a plurality of windows and a porous coating configured to promote bone ingrowth of the humerus onto the collar. In some embodiments, forming the collar to have an outer ring and a central portion such that the plurality of windows, together, have a substantially circular shape interrupted by portions of the collar coupling the outer ring and the central portion. In some embodiments, the method includes forming the collar to have a substantially circular shape. In some embodiments, the method includes disposing a porous coating on the at least one fin. In some embodiments, the porous coating comprises pores of varying sizes, thereby aiding in apposition of bone ingrowth.

In some other embodiments, a kit surgical kit for shoulder arthroplasty is provided. The kit includes a plurality humeral implants, each having a plurality of fins, wherein at least one fin of each of the plurality humeral implants comprises a serrated bottom edge.

In some embodiments, each of the plurality of humeral implants has a different size. In some embodiments, larger size implants are associated with fins that protrude relatively farther from the centerline compared to larger size implants. In some embodiments, each of the plurality of humeral implants comprises a collar having a same size. In some embodiments, each of the plurality of humeral implants comprises a central body having a same size. In some embodiments, on a largest size implant, the plurality of fins extend radially relatively farther away from the central body compared to smaller size implants. In some embodiments, on a largest size implant, the plurality of fins extend distally relatively farther beyond the central body compared to smaller size implants. In some embodiments, on a largest size implant, the plurality of fins comprise relatively more serrated points compared to smaller size implants. In some embodiments, on a largest size implant, an angle between a medial edge and the serrated bottom edge of the at least one fin is relatively smaller compared to smaller size implants.

BRIEF DESCRIPTION OF THE DRAWINGS

A more complete appreciation of the subject matter of the present disclosure and of the various advantages thereof can be realized by reference to the following detailed description in which reference is made to the accompanying drawings in which:

FIG. 39 illustrates an exploded perspective view of an implant system for a shoulder arthroplasty, in accordance with some example embodiments;

FIG. 40 illustrates a perspective view of the condensed implant system of FIG. 39, in accordance with some example embodiments;

FIG. 43 illustrates a side view of instrumentation for a threaded stem-insertion approach, in accordance with some example embodiments;

FIG. 44 illustrates a side view of instrumentation for a non-threaded stem-insertion approach, in accordance with some example embodiments;

DETAILED DESCRIPTION

Implementations of the technology described herein are directed generally to shoulder arthroplasty. The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Figure 62:
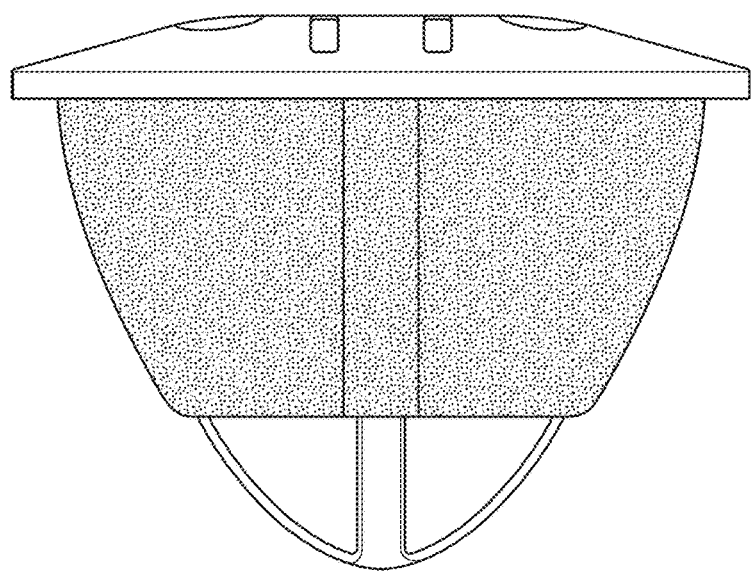
FIG. 62 illustrates an example humeral stem.
Figure 63:
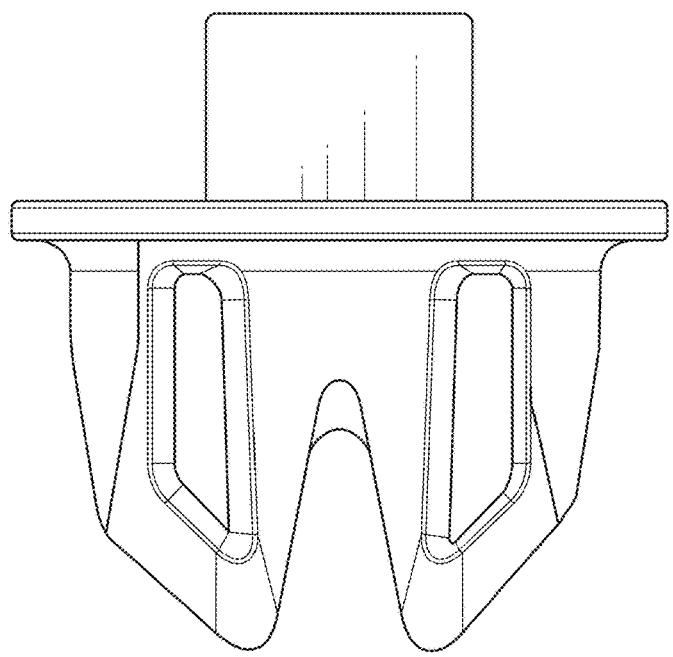
FIG. 63 illustrates another example humeral stem.
Figure 64:
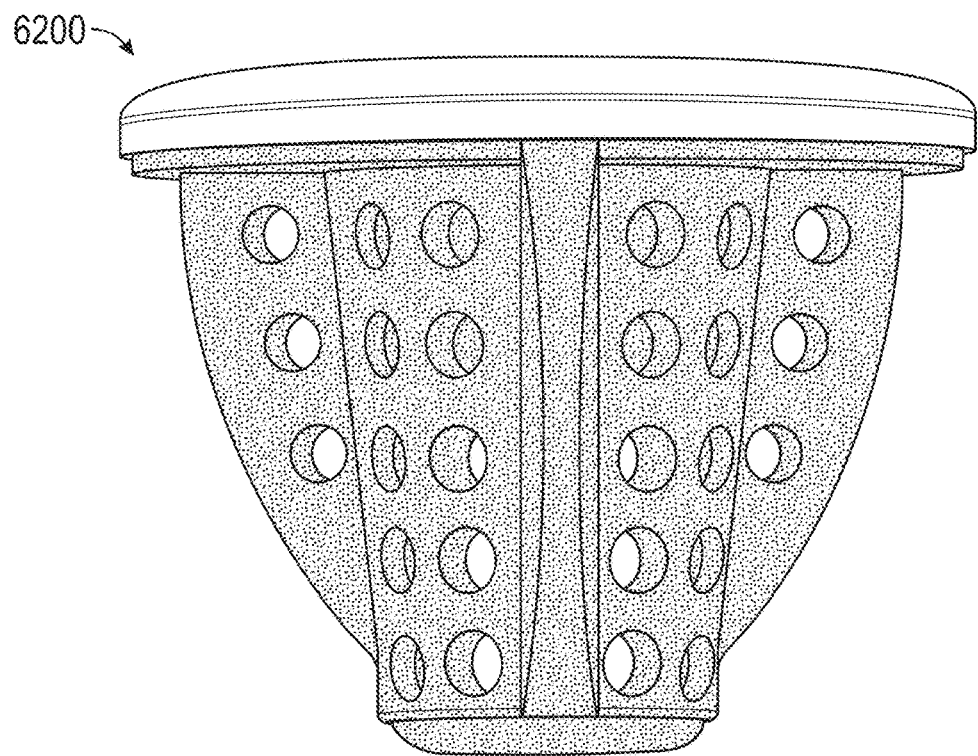
FIG. 64 illustrates yet another example humeral stem.
Figure 65:
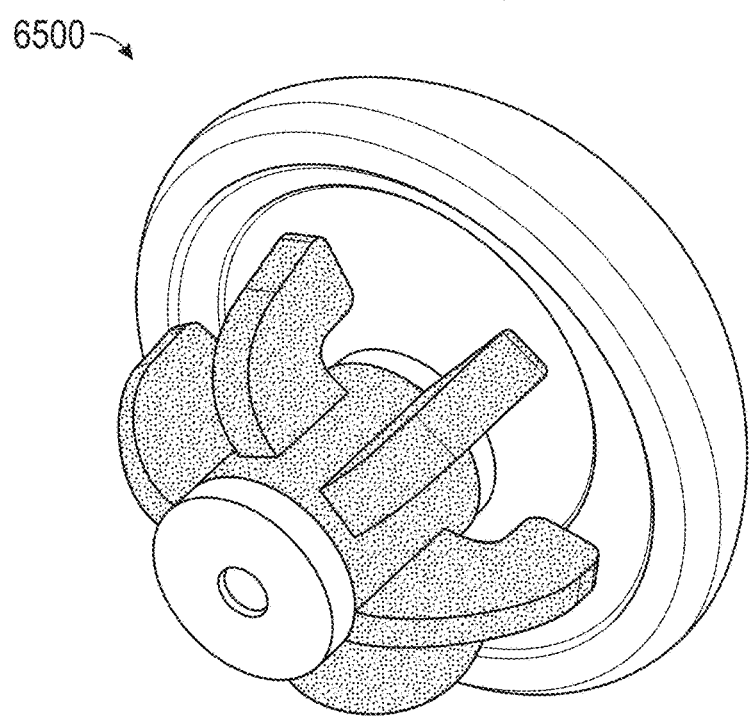
FIG. 65 illustrates yet another example humeral stem.
Figure 66:
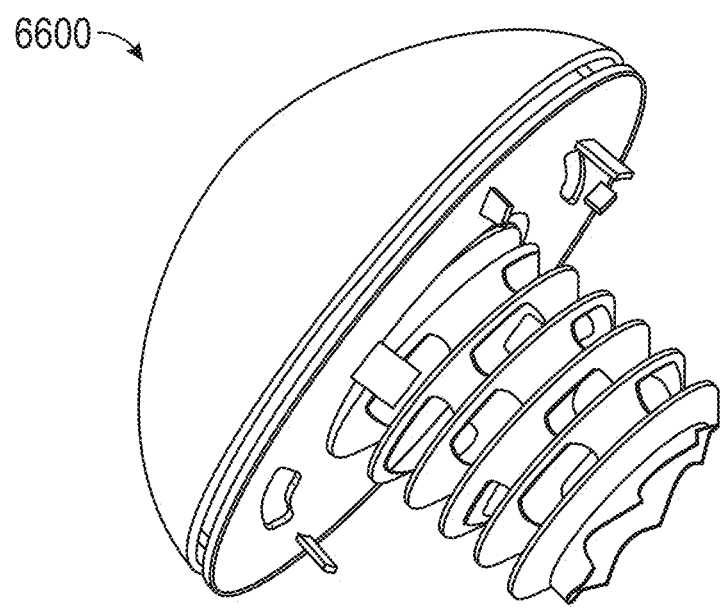
FIG. 66 illustrates yet another example humeral stem.

A need exists for implants, systems and/or kits for shoulder arthroplasty, and associated methods, that allow for sparing of bone while also providing the ability for easy revision surgery. Surgical implementations utilizing humeral canal-sparing, cementless implants first came out in Europe in 2004, but have not been available in the United States until 2015. There are currently five stemless implant devices that have been cleared in the United States: the Wright/Tornier Simpliciti K143552 (see FIG. 62), the Simmer Sidus K171858 (see FIG. 63), the Exactech Equinoxe Stemless K173388 (see FIG. 64), the Simmer Biomet Nano K182516 (see FIG. 65) and the Arthrex Eclipse K183194 (see FIG. 66).

In contrast to these implants, the present implementations provide new solutions for patients having good bone quality with bone-sparing solutions for anatomic total shoulder arthroplasty. One advantage afforded such new implants is a multi-fin, serrated or stepped edge that both cuts into and compacts bone at the osteotomy site to provide a tighter cementless press-fit between the implant and the bone in which it is anchored. Another advantage afforded such new implants is the use of porous coating that may include variability in pore sizes, similar to a "lava rock" type of structure, that aids in the apposition of bone for excellent in-growth results and may be used as the main method of metaphyseal fixation, for example, on a humeral stem. Surgical kits may also be provided with multiple sized stem implants wherein, on those implants with larger size stems, the fins may protrude farther from an axial centerline to provide additional stability with a fit and fill specification.

Advantages and/or beneficial aspects of the new canal-sparing embodiments described herein include, but are not limited to, maximal preservation of bone, reduced periprosthetic fractures, reduction in stress shielding, flexibility of altered anatomy, easier and less complex revision surgery at least partly due to the utilization of windows in a collar of the stem implants. Of particular importance with respect to less bone removal is less soft tissue trauma, less post-operative pain, a quicker operation, and a shorter recover period. Moreover, the new canal-sparing embodiments described herein benefit from humeral fit analysis to optimize implant fit in the humeral metaphysis. At least one aspect of such optimized implant fit is a design that specifically targets denser-boned peripheral zones of the proximal humerus. For example, compacted bone of the peripheral regions of the proximal humerus surrounding fins of the stem implant, as will be described in more detail below, have a higher density compared to more central, medial regions of the proximal humerus. The utilization of implants having fins with angled, serrated or stepped edges and/or tips as described anywhere herein offers surgeons the ability to use the implant itself to cut into bone and push cancellous bone outward, thereby compacting the bone surrounding the press-fit, porous fins and providing an enhanced cementless, press fit. Although the implant is described herein as "cementless," the use of cement is not precluded, and there may be applications where a surgeon might use cement in conjunction with the implants described herein.

One or more embodiments of a surgical implant, surgical implant system and/or surgical implant kit for performing a shoulder arthroplasty will now be described in connection with an example humeral osteotomy and shoulder arthroplasty.

As will be described in more detail below, such an example humeral osteotomy and shoulder arthroplasty may include one or more of the following general procedures and/or steps: performing the osteotomy cut of the humeral head (for example as described in connection with at least FIGS. 1-4), selecting a head size and inserting a guide pin through an aperture for a cannulated approach (for example as described in connection with at least FIGS. 5-8), cleaning up the osteotomy surface using a planer (for example as described in connection with at least FIG. 9), preparing for a collar and central body of a stem using a collar reamer and, in some cases, a core drill (for example as described in connection with at least FIGS. 13, 14, 18 and 19), optionally preparing the metaphysis of the osteotomy for the bone-cutting and/or compacting fins of the stem using bone-compacting punches (for example as described in connection with at least FIGS. 20-24), trialing humeral heads from either or both of the AltiVate Anatomic and/or Turon systems utilizing one or more adapters configured to allow conversion between the systems (for example as described in connection with at least FIGS. 28-36), back-table assembly of the humeral head and neck implant (for example as described in connection with at least FIGS. 38-42), two methods of stem insertion using a threaded stem inserter or a non-threaded stem inserter (for example as described in connection with at least FIGS. 43-46 for stems as described in connection with at least FIGS. 53-61), and final implantation of the assembly of the head/neck assembly to the stem in-situ (for example as described in connection with at least FIG. 47), wherein additional instrumentation may be provided to aid in revision of the implant, if needed (for example as described in connection with at least FIGS. 48-52).

Humeral Preparation for Osteotomy

Figure 1:
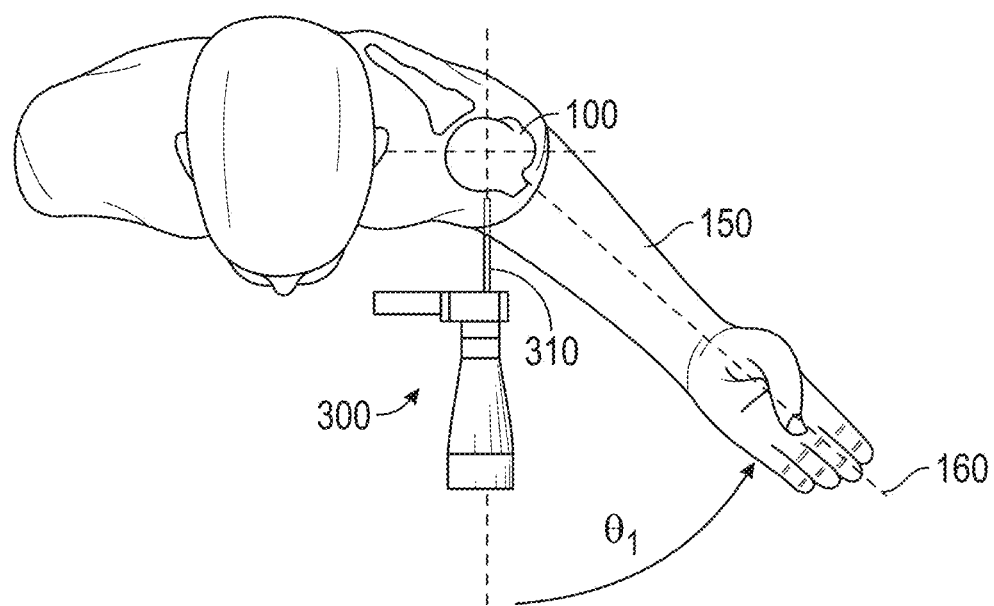
FIG. 1 illustrates a top view of a patient undergoing a shoulder arthroplasty, in accordance with some example embodiments.

FIG. 1 illustrates a top view of a patient undergoing a shoulder arthroplasty, in accordance with some example embodiments. A proximal humerus 100 of the patient is exposed and prepared for shoulder arthroplasty. In some embodiments, such preparation can include trimming osteophytes from proximal humerus 100 utilizing, for example, a rongeur to improve visualization of the anatomic neck of proximal humerus 100.

An extramedullary osteotomy guide 300 can be positioned onto the anterior humeral shaft and a varus-valgus angle of the humeral head osteotomy may be determined.

Figure 3:
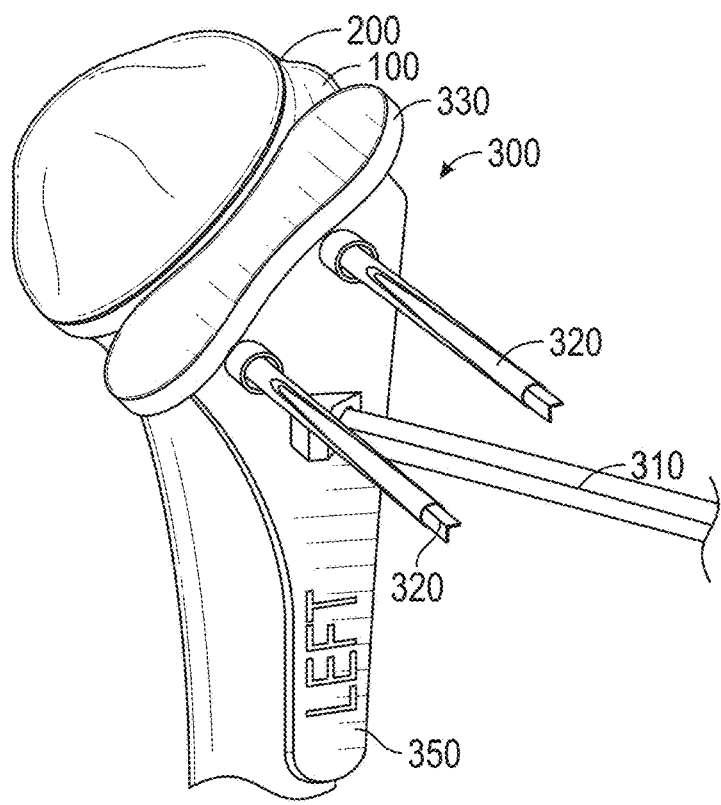
FIG. 3. Illustrates a perspective view of an osteotomy guide, in accordance with some example embodiments.

FIG. 3 illustrates a perspective view of guide 300 positioned on proximal humerus 100. Guide 300 comprises a body 350 configured to be disposed on a side of proximal humerus 100. Guide 300 may further comprise one or more of an alignment rod 310, one or more bone pins 320, a cutting guide surface 330, and/or one or more orientation markings on one or both sides. For example, guide 300 can include a "right" label, imprint, emboss or other suitably identifying marking on a first side that faces outward when guide 300 is properly positioned on a right humerus and/or a "left" label, imprint, emboss or other suitably identifying marking on a second side that faces outward when guide 300 is properly positioned on a left humerus.

Figure 2:
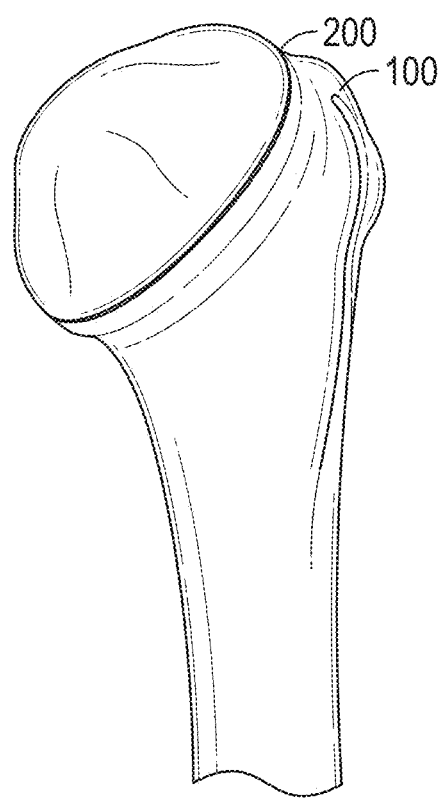
FIG. 2 illustrates a perspective view of a preferred height of an osteotomy of a proximal humerus, in accordance with some example embodiments.

A proper height of the osteotomy, at the anatomic neck of proximal humerus 100, is illustrated in FIG. 2 at an intersection 200 between a medial portion of the rotator cuff footprint and the articular surface.

As illustrated in FIG. 1, the forearm 150 of the arm receiving the shoulder arthroplasty can be positioned in a desired orientation, for example, externally rotated to 01=approximately 30° of retroversion. However, the present disclosure is not so limited and any appropriate, desired orientation is also contemplated. Alignment rod 310 of guide 300 can be aligned parallel to a direction of extension 160 of forearm 150, as shown by the arrow in FIG. 1. Guide 300 can then be secured to proximal humerus 100 by advancing one or more bone pins 320 through a side of guide 300 and into proximal humerus 100 utilizing, for example, a pin driver (not shown). A portion of the humeral head may be resected by cutting proximal humerus 100 parallel to cutting guide surface 330 until the portion is completely resected. Upon completion of the bone resection, pin(s) 320 may be removed, for example utilizing a bone pin extractor (not shown), and guide 300 may be removed from proximal humerus 100.

Figure 4:
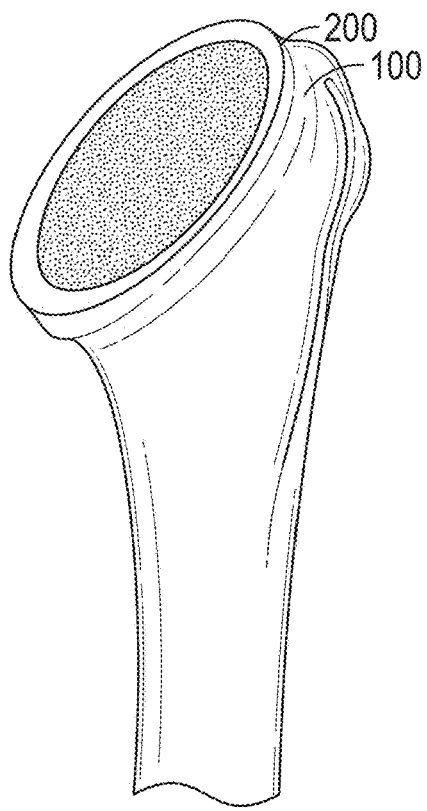
FIG. 4 illustrates a perspective view of a proximal humerus after an osteotomy of a preferred height has been performed, in accordance with some example embodiments.

FIG. 4 illustrates a perspective view of proximal humerus 100 having the portion thereof properly resected. Evaluation of the bone quality at the resection can be performed. In some embodiments, the "thumb test" (e.g., pressing the thumb into the exposed bone to assess relative give) can be utilized to determine whether the bone quality is sufficiently sturdy for stemless shoulder arthroplasty.

Head Size Selection and Guide Pin Insertion—Humeral Preparation

A system for shoulder arthroplasty can include one or more variable thickness neutral humeral head trials 500 to, for example, optimize medial-lateral and soft tissue tension. An appropriately sized head trial can be selected such that head trial 500 covers the resection cut and substantially recreates the native anatomy of proximal humerus 100 without overstuffing.

Figure 5:
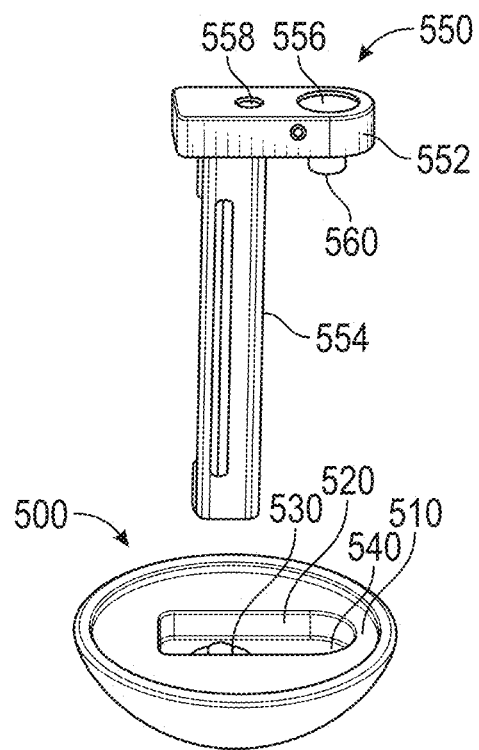
FIG. 5 illustrates a perspective view of a humeral head trial and pin guide, in accordance with some example embodiments.

As illustrated in FIG. 5, humeral head trial 500 comprises a substantially flat bottom surface 510, a recess 520 in bottom surface 510, a first aperture 530 and a second aperture 540, both disposed in recess 520 and extending completely through humeral head trial 500, and a convex top surface.

A pin guide 550 is configured to be disposed in recess 520 and extend through first aperture 530. Pin guide 550 may comprise a body 552 and a shaft 554 extending away from body 552. Body 552 comprises a first aperture 556 configured to receive a screw 560 for securing pin guide 550 within second aperture 540 in recess 520 in bottom surface 510 of humeral head trial 500 and a second aperture 558 configured to receive a guide pin 800 (see, e.g., FIG. 8). Second aperture 558 extends axially through shaft 554 of pin guide 550. As will become more apparent through the description below, such a design allows guide pin 800 to be centered while simultaneously sizing the humeral head, a trial and/or an implant.

Figure 6:
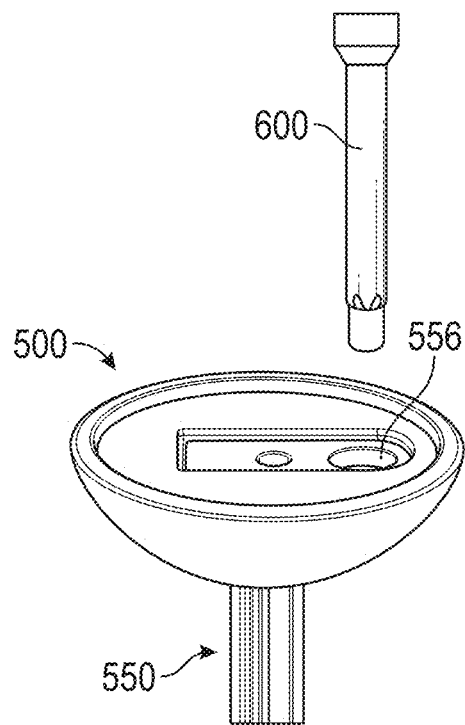
FIG. 6 illustrates a perspective view of an assembly of the pin guide and humeral head trial of FIG. 5, in accordance with some example embodiments.

As illustrated in FIG. 6, screw 560 may be threaded through first aperture 556 of pin guide 550 and into second aperture 540 of humeral head trial 500 to, thereby, secure pin guide 550 within recess 520 of humeral head trial 500 utilizing, for example, a driver 600. Accordingly, shaft 554 of pin guide 550 extends away from the convex top surface of humeral head trial 500.

Figure 7:
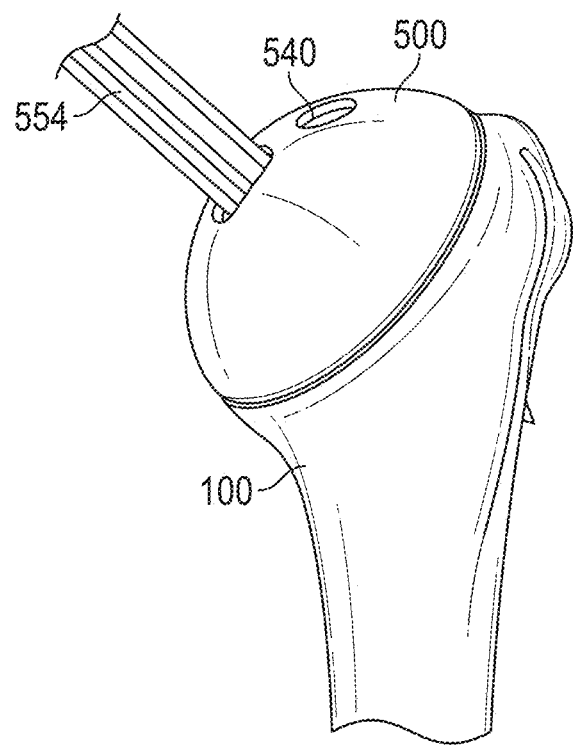
FIG. 7 illustrates a perspective view of the assembly of FIG. 6 disposed on the proximal humerus, post-osteotomy, in accordance with some example embodiments.

As illustrated in FIG. 7, coupled humeral head trial 500 and pin guide 550 can be centered on the osteotomy of proximal humerus 100 and guide pin 800 (see, e.g., FIG. 8) may be inserted through second aperture 558, e.g., cannula, of pin guide 550 (see, e.g., FIG. 5) and into proximal humerus 100. In some embodiments, perforating cortical bone of proximal humerus 100 with guide pin 800 without utilizing an "up and down" plunging motion is desirable for maintaining stability of guide pin 800 in proximal humerus 100. Overpenetration of guide pin 800 into soft tissue should also be avoided in order to protect the axillary nerve from damage.

Figure 8:
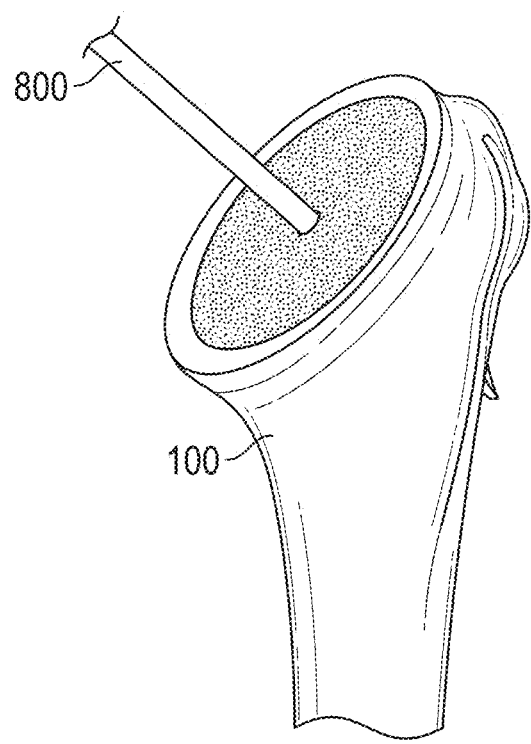
FIG. 8 illustrates the proximal humerus having a guide pin inserted into the osteotomy, in accordance with some example embodiments.

As illustrated in FIG. 8, leaving guide pin 800 in proximal humerus 100, humeral head trial 500 and pin guide 550 can be removed over guide pin 800. Re-evaluation of bone quality and stability of guide pin 800 may now be performed. In some embodiments, a retractor (not shown) can be placed at a guide pin 800 exit region of the shoulder to prevent soft tissue damage.

Humeral Planing—Humeral Preparation

Figure 9:
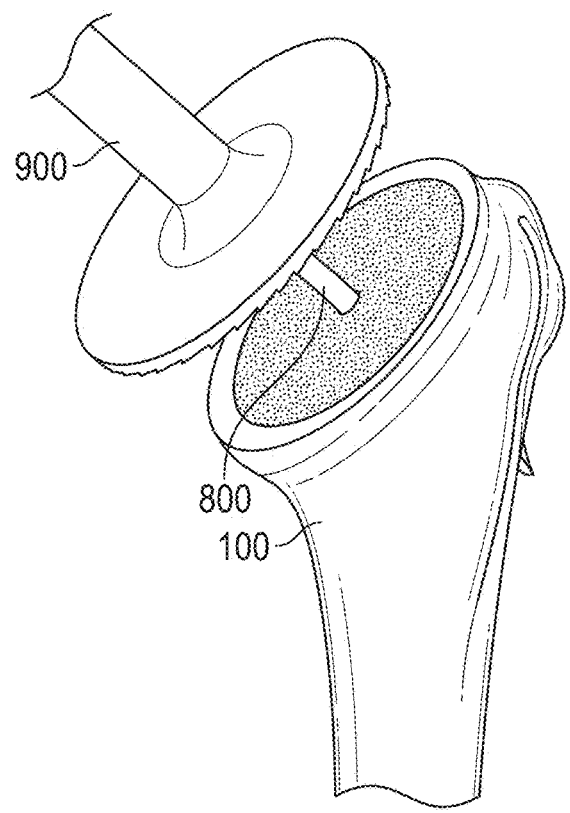
FIG. 9 illustrates a humeral planer disposed on the guide pin of FIG. 8, in accordance with some example embodiments.

In some implementations, the osteotomy can be fine-tuned utilizing a humeral planer 900 (see, e.g., FIG. 9). In some such implementations, humeral planer 900 may be provided in a plurality of sizes (e.g., small, medium and large) and the appropriate size may be selected and inserted over guide pin 800 such that a planing surface of planer 900 is disposed on an exposed surface of the osteotomy. Accordingly, humeral planer 900 may be cannulated, e.g., comprising a central aperture (not shown in FIG. 9) configured to receive guide pin 800 therethrough. Under power, humeral planer 900 can be carefully advanced while periodically monitoring the osteotomy surface. To ensure smooth operation of humeral planer 900, its cutting teeth may be periodically cleaned to remove excess bone as needed. To further reduce collateral bone damage, these cutting teeth may have a bone conserving design. Once a desired amount of bone has been removed and the osteotomy surface is sufficiently even, humeral planer 900 can be removed over guide pin 800.

Implant Size Assessment

Selecting an appropriately sized humeral stem can be performed with the aid of one or more of a centering guide 1000 and x-ray templates. For example, x-ray templates, in either digital or physical form, may be utilized to preoperatively assess and select an appropriately sized humeral implant.

Figure 10:
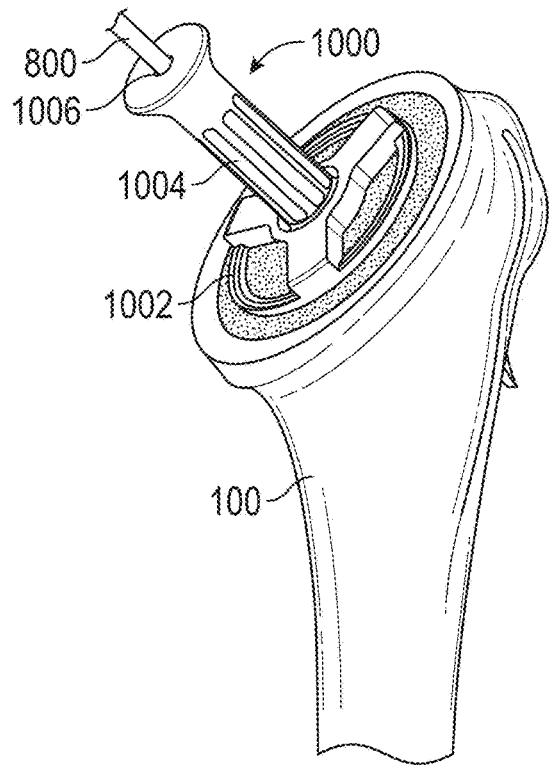
FIG. 10 illustrates a centering guide disposed on the guide pin of FIG. 8, in accordance with some example embodiments.
Figure 11:
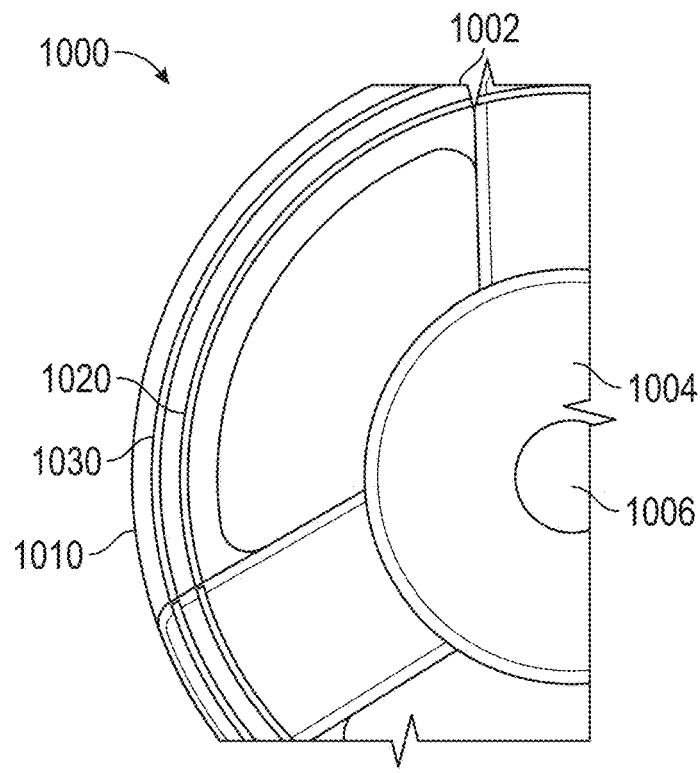
FIG. 11 illustrates a magnified partial view of the centering guide of FIG. 10, in accordance with some example embodiments.
Figure 12:
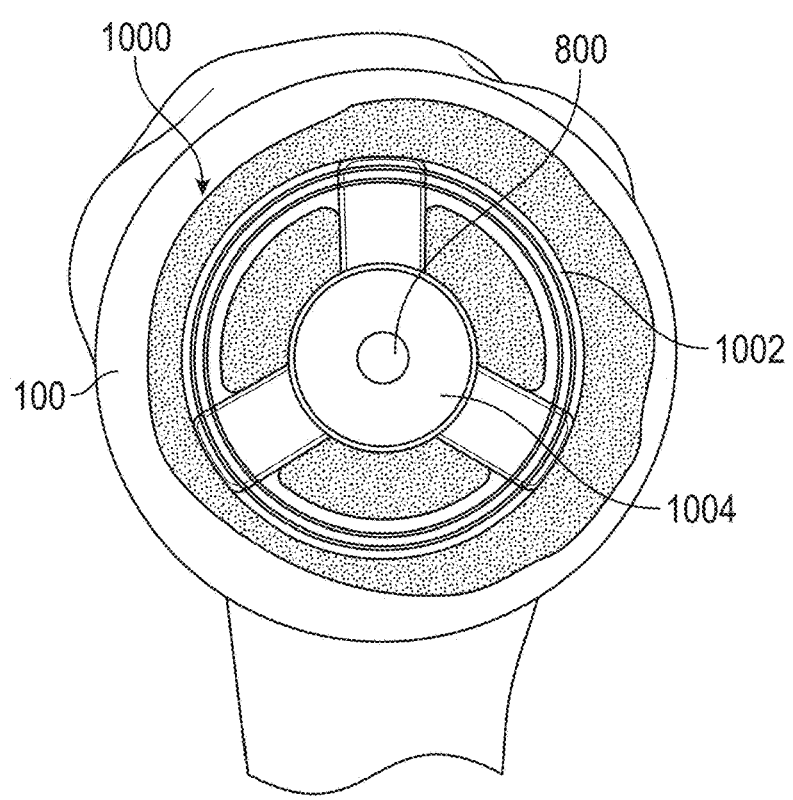
FIG. 12 illustrates an on-axis view of the centering guide of FIG. 10, in accordance with some example embodiments.
Figure 13:
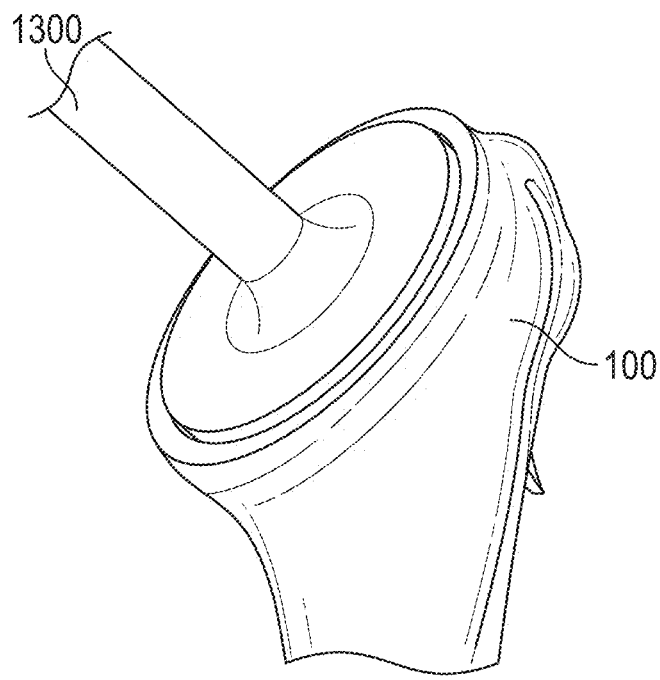
FIG. 13 illustrates a perspective view of collar reamer disposed on the guide pin of FIG. 8, in accordance with some example embodiments.

FIG. 10 illustrates a perspective view of centering guide 1000 disposed on guide pin 800, in accordance with some embodiments, while FIG. 12 illustrates a top view of centering guide 1000 on guide pin 800, and FIG. 11 illustrates a magnified partial top view of centering guide 1000. As illustrated in FIGS. 10-12, centering guide 1000 is configured to fit within the prepared bone below the humeral head resection plane and provides a respective reference for each of a plurality of different humeral stem implant sizes (e.g., small, medium and large). For example, centering guide 1000 comprises a circular base 1002 and a shaft 1004 extending away from circular base 1002. Shaft 1004 comprises a central aperture 1006 configured to receive guide pin 800 therethrough.

In some embodiments, an outer diameter 1010 of circular base 1002 is the same as an outer diameter of each of the plurality of differently sized humeral stem implants 5300, 5300*a-c* (see, e.g., FIGS. 53-61), as will be described in more detail below. In addition, circular base 1002 can comprise a first marking 1020 corresponding to a radial position of a plurality of fins of, e.g., the small size humeral stem implant 5300*c*, a second marking 1030 corresponding to a radial position of a plurality of fins of, e.g., the medium size humeral implant 5300*b*, while outer diameter 1010 can also correspond to a radial position of a plurality of fins of, e.g., the large size humeral implant 5300*a*.

In some embodiments, centering guide 1000 is also configured for pre-assessment of a position of humeral stem 5300 within the humeral metaphysis and, in particular, assessment of potential for peripheral cortical contact with the humeral stem.

Stem Implant Preparation—Humeral Preparation

Figure 14:
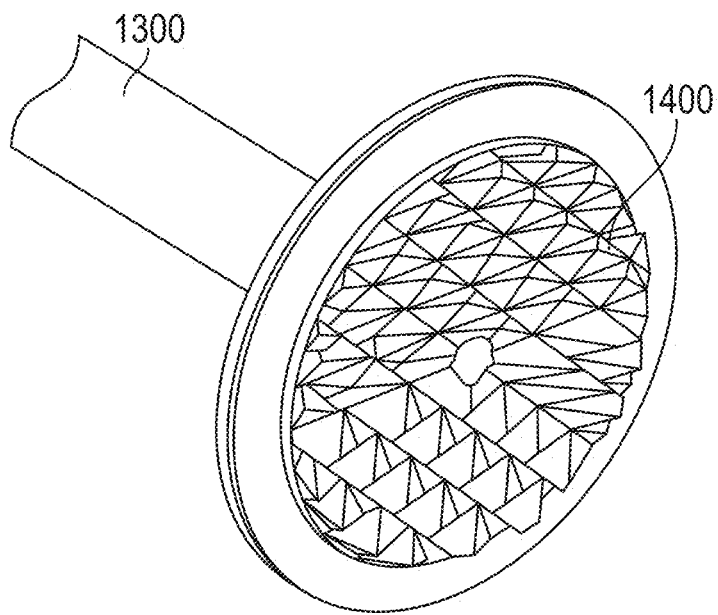
FIG. 14 illustrates a perspective view of teeth of the collar reamer of FIG. 13, in accordance with some example embodiments.
Figure 15:
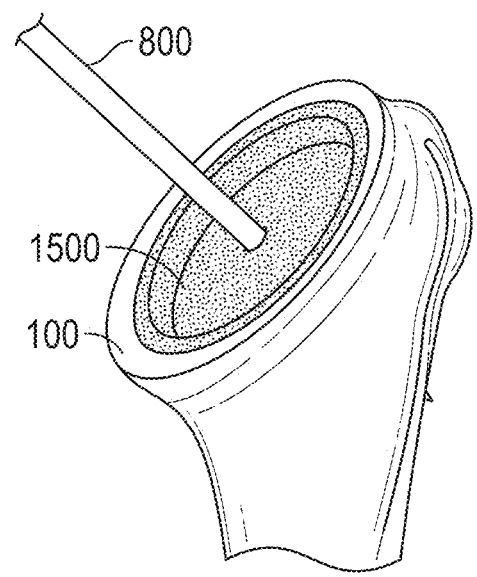
FIG. 15 illustrates a perspective view of the proximal humerus, post-reaming, in accordance with some example embodiments.

Proximal humerus 100 may be prepared for the implant collar by inserting a collar reamer 1300 over guide pin 800 (see, e.g., FIG. 13) and reaming proximal humerus 100 to the physical stop of collar reamer 1300, thereby forming a recess 1500 in the osteotomy of proximal humerus 100 (see, e.g., FIG. 15). FIG. 14 illustrates a perspective view of example teeth 1400 of collar reamer 1300. To ensure smooth operation of collar reamer 1300, teeth 1400 may be periodically cleaned to remove excess bone as needed. To further reduce collateral bone damage, teeth 1400 may have a bone conserving design.

Figure 16:
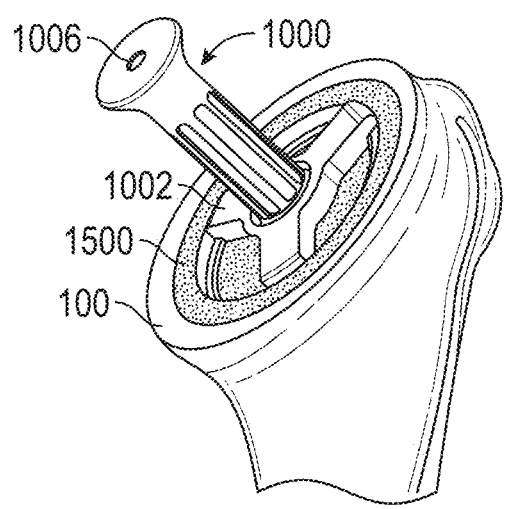
FIG. 16 illustrates a perspective view of the centering guide disposed in a recess formed by the collar reamer of FIG. 13, in accordance with some example embodiments.
Figure 17:
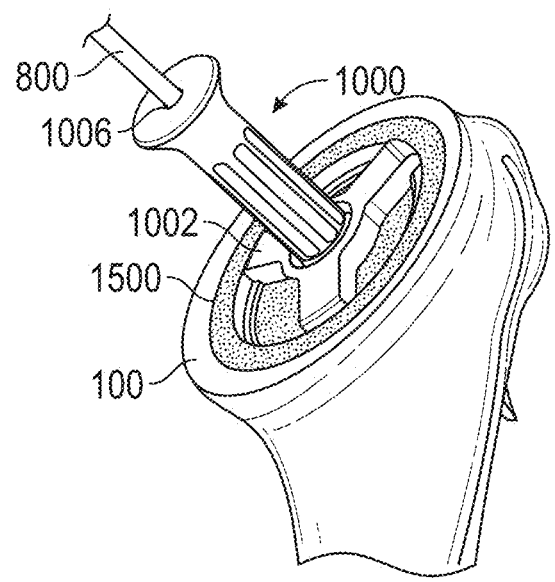
FIG. 17 illustrates a perspective view of the centering guide as in FIG. 16, further illustrating the guide pin re-installed in the proximal humerus, in accordance with some example embodiments.

In some cases, instrument changes over guide pin 800 may lead to inadvertent removal of guide pin 800. In such cases, centering guide 1000 is also configured to provide a guide for re-insertion of guide pin 800, as illustrated in at least FIGS. 16 and 17. Specifically, an outer diameter of circular base 1002 of centering guide 1000 is sized to sit snuggly within recess 1500 and allow for proper re-alignment re-insertion of guide pin 800 along its original trajectory through center aperture 1006.

Figure 18:
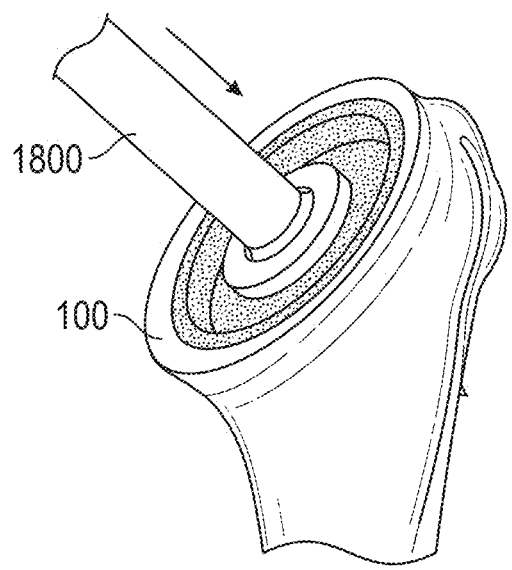
FIG. 18 illustrates a perspective view of a core drill disposed within the recess formed by the collar reamer of FIG. 13, in accordance with some example embodiments.
Figure 19:
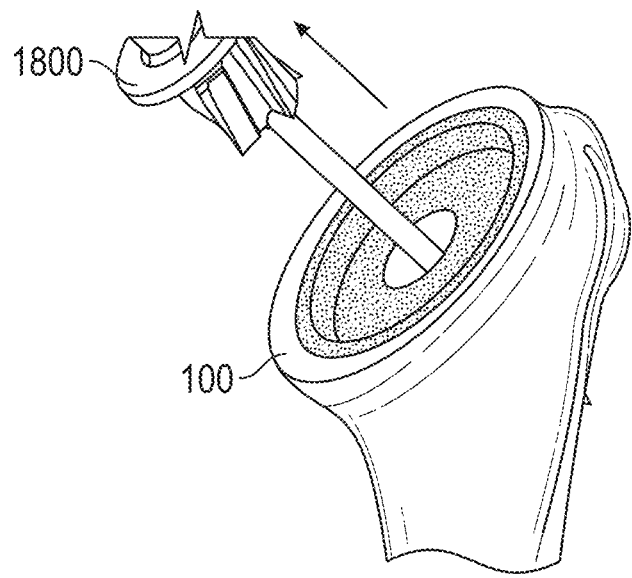
FIG. 19 illustrates a perspective view of the core drill of FIG. 18 pulled back from the recess, in accordance with some example embodiments.

In some implementations, a core drill 1800 and/or an appropriately sized humeral punch 2000 may be optionally utilized based on the surgeon's desired level of frictional press-fit for ultimate implant insertion. Core drill 1800 may comprise typical cutting flutes and may be cannulated such that it may be inserted over guide pin 800 and a core drilled out of proximal humerus 100 to the physical stop (e.g., the desired depth), as illustrated in FIG. 18. Core drill 1800 may then be removed over guide pin 800, as illustrated in FIG. 19.

Figure 20:
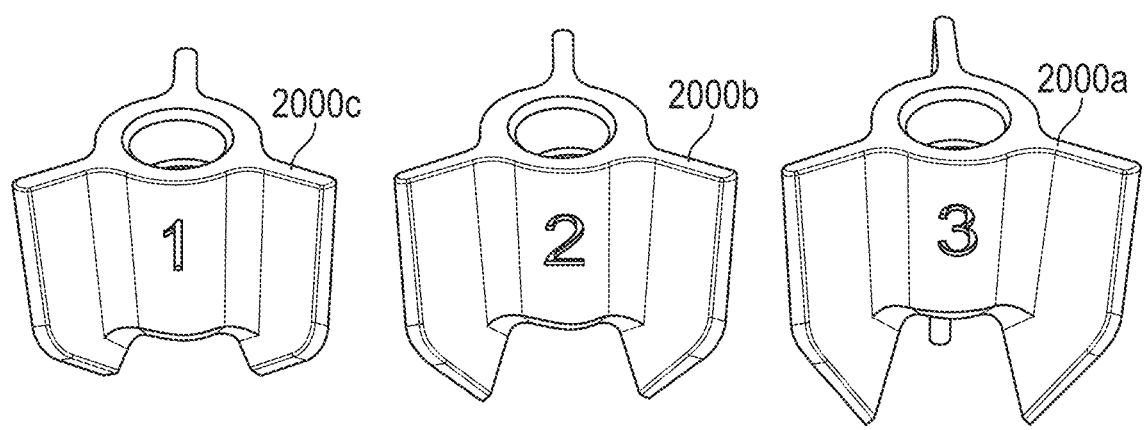
FIG. 20 illustrates a perspective view of a plurality of punches having different sizes, in accordance with some example embodiments.

As illustrated in FIG. 20, humeral punch 2000 may come in a plurality of different sizes, e.g., large 2000*a*, medium 2000*b* and small 3000*c*, each having fins of a particular shape and size corresponding to the particular shape and size of stem 5300 (see, e.g., FIGS. 53-61). As illustrated, punch 2000 comprises minimal cutting edges to allow for greater bone compaction, which can help to artificially increase the density of the bone that will be immediately adjacent stem 5300 after implantation. In some embodiments, humeral punch 2000 may be color-coded, stamped or otherwise marked to correspond with its fins' relative sizes, e.g., small 2000*c* is gold, medium 2000*b* is bronze, and large 2000*a* is black. The surgeon may select the desired humeral implant size and attach the correspondingly sized and/or colored humeral punch 2000 (see, e.g., FIG. 20) to a punch inserter handle 2100 (see, e.g., FIG. 21), taking care not to over-tighten punch 2000 on handle 2100. In some cases, for medium and/or large sized humeral implants where a greater frictional press-fitting is desired, humeral punch 2000 may be selected one size smaller than the appropriately sized humeral implant.

Figure 21:
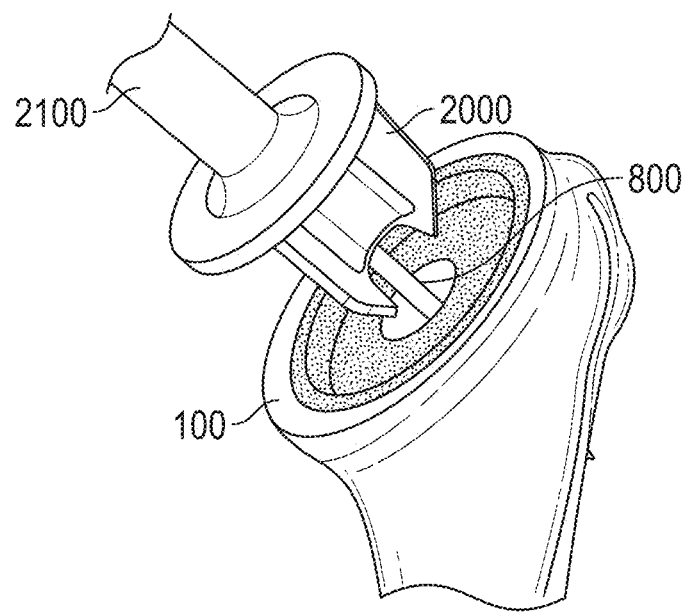
FIG. 21 illustrates a perspective view of a punch and attached handle disposed over the guide pin of FIG. 8, in accordance with some example embodiments.
Figure 22:
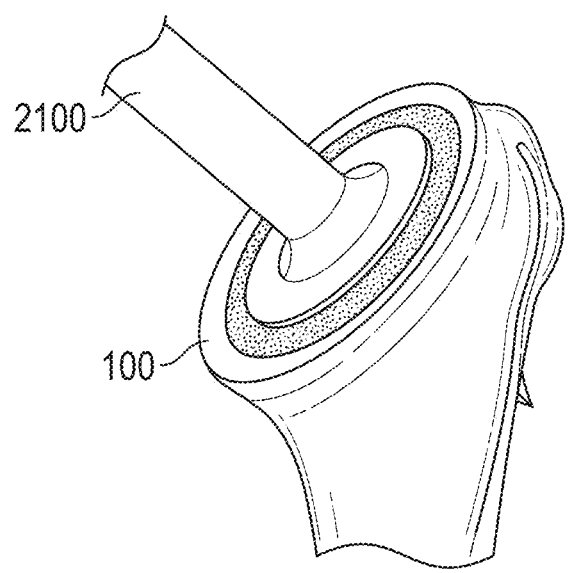
FIG. 22 illustrates a perspective view of the punch of FIG. 21 implanted in the osteotomy of the proximal humerus, in accordance with some example embodiments.

Humeral punch 2000 and handle 2100 may be cannulated, e.g., having an aperture allowing insertion over guide pin 800 and alignment of one fin superolaterally (see, e.g., FIG. 21). Accordingly, humeral punch 2000 and handle 2100 may each be cannulated, e.g., having a central aperture through which guide pin 800 is configured to extend. Once on guide pin 800, handle 2100 may be gently impacted with a mallet until a top face of handle 2100 is flush with the osteotomy (see, e.g., FIG. 22). Accordingly, the top face of the portion of handle 2100 directly coupling humeral punch 2000 allows for visual representation of a depth of implantation of humeral punch 2000. Upon reaching this flush position, handle 2100 may be gently unthreaded from punch 2000 while punch 2000 is inserted in proximal humerus 100. Punch 2000 should be flush with a bottom surface of recess 1500 created by collar reamer 1500. Guide pin 800 may then be removed (see, e.g., FIG. 24).

Figure 23:
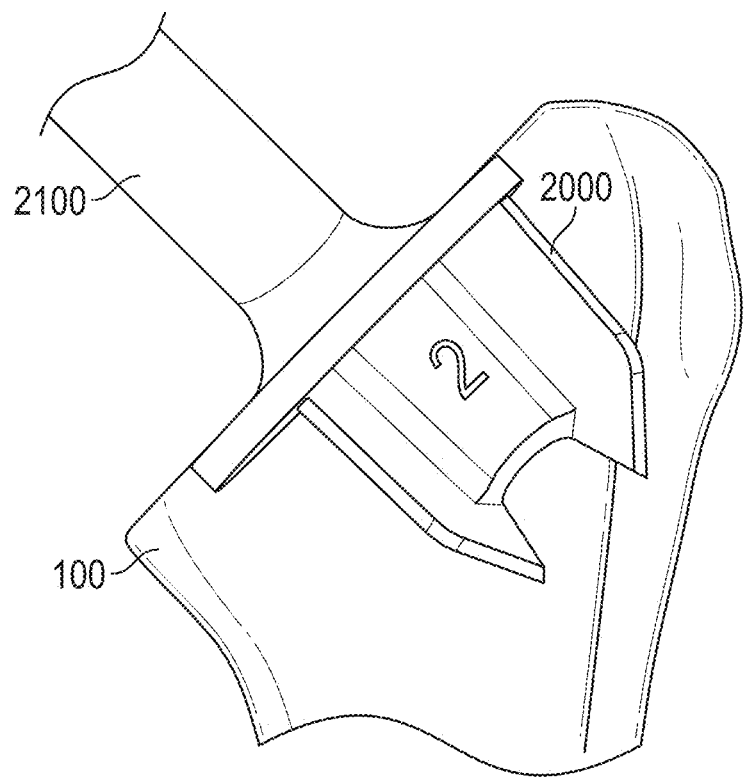
FIG. 23 illustrates a side view of the punch and attached handle of FIG. 21 disposed to one side of the proximal humerus, in accordance with some example embodiments.
Figure 24:
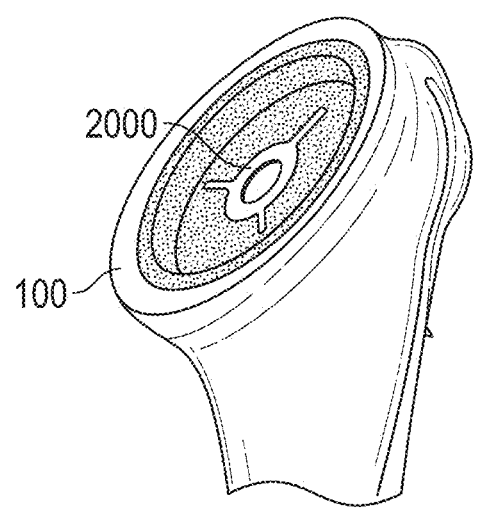
FIG. 24 illustrates a perspective view of the punch of FIG. 21 implanted in the osteotomy of the proximal humerus with handle removed, in accordance with some example embodiments.

As illustrated in FIG. 23, assembled humeral punch 2000 and handle 2100 can also be held over the humeral metaphysis along the osteotomy (e.g., along a size of the proximal humerus 100 and osteotomy) to reference the humeral implant fit in the metaphysis.

As will be described in more detail below, punch inserter handle 2100 may also be configured to couple and/or mate with a non-threaded stem impactor 4450, for example, as will be described in connection with at least FIG. 44, and with a neck impactor 4250, for example, as will be described in connection with at least FIG. 42. Such cross-compatibility and/or interchangeability provides for streamlined instrumentation and reduces preparation time.

In cases where the surgeon opts to utilize core drill 1800 and humeral punch 2000, it is desirable to utilize core drill 1800 first. In cases where the surgeon opts to utilize core drill 1800 and not appropriately sized humeral punch 2000, it is desirable to score the bone with punch 2000 to ensure proper position and alignment of the stem implant with the prepared surgical site during final implantation.

Humeral Protection

Figure 25:
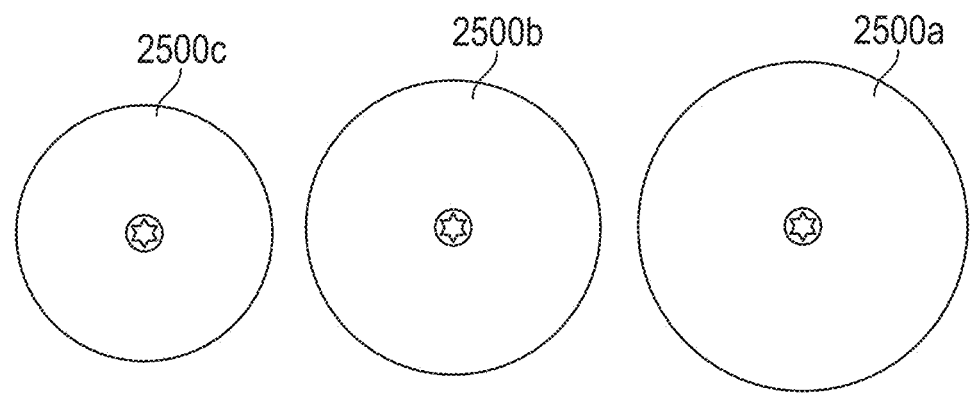
FIG. 25 illustrates a top view of a plurality of humeral protectors, each having a different size, in accordance with some example embodiments.
Figure 26:
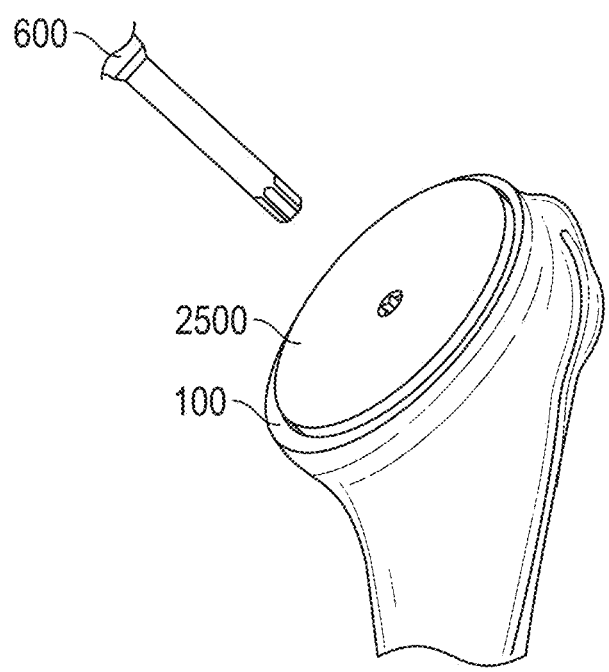
FIG. 26 illustrates one of the humeral protectors of FIG. 25, disposed against the osteotomy of the proximal humerus, in accordance with some example embodiments.
Figure 27:
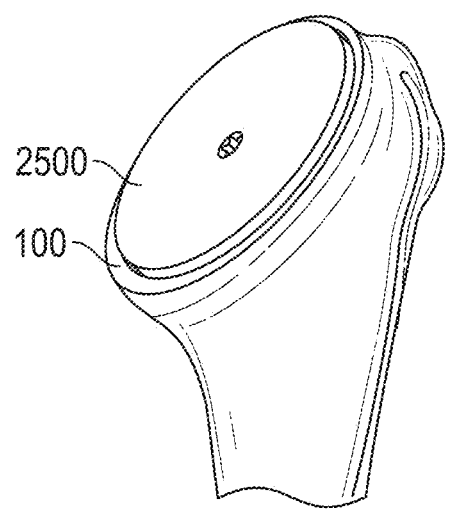
FIG. 27 illustrates the humeral protector of FIG. 26 secured to the proximal humerus, in accordance with some example embodiments.
Figure 28:
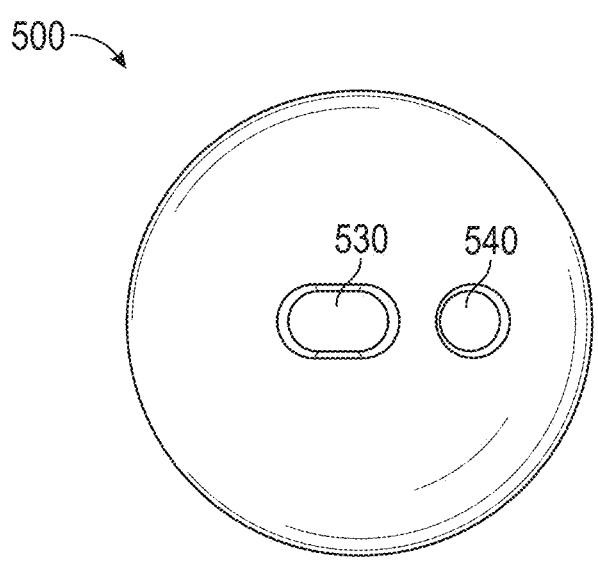
FIG. 28 illustrates a top view of a humeral head trial, in accordance with some example embodiments.

After site preparation, the osteotomy may be covered and protected by threading an appropriately sized humeral protector 2500 to humeral punch 2000 (see, e.g., FIGS. 25-27). Humeral protector 2500 may aid in maintaining the humeral metaphyseal integrity during glenoid preparation. As illustrated by FIG. 25, humeral protector 2500 can be provided in a plurality of sizes (e.g., small or 35 millimeters (mm) 2500*c*, medium or 40 mm 2500*b* and large or 45 mm 2500*a*), each corresponding to a different sized punch 2000*a-c*. The mono-block, or unitary, design of humeral protector 2500 provides for quick assembly. As illustrated in FIG. 26, driver 600 (e.g., a straight Torx driver) may be utilized to couple and/or uncouple humeral protector 2500 and punch 2000.

Humeral Trialing

Figure 32:
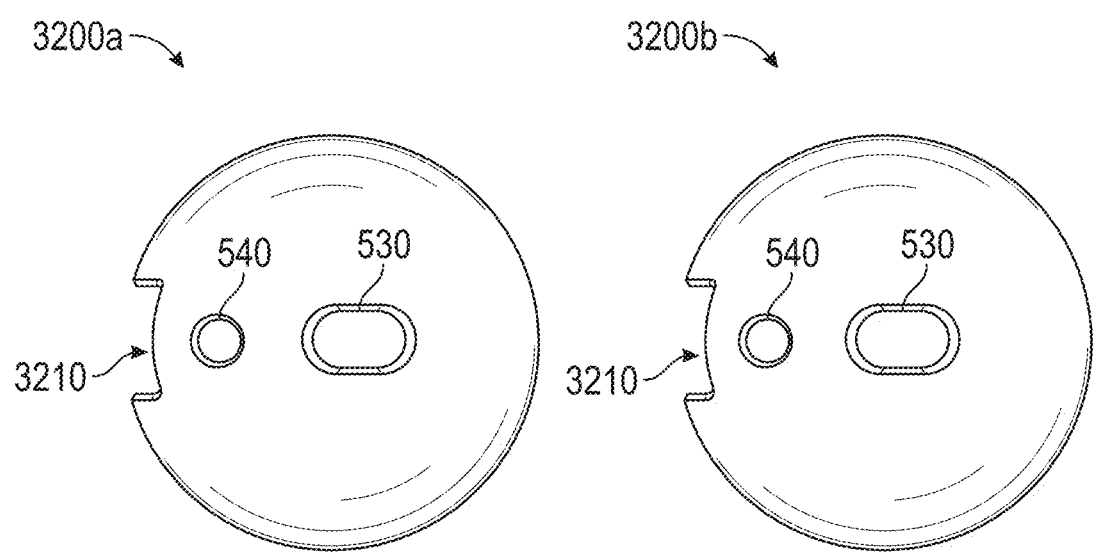
FIG. 32 illustrates a top view of two alternative humeral head trials, in accordance with some example embodiments.

As previously described in connection with at least FIGS. 5-7, a system for performing shoulder arthroplasty may include variable thickness humeral heads 500, e.g., of an Altivate™ Anatomic Shoulder System, may also be compatible with systems for shoulder arthroplasty as described anywhere herein. Further examples of a humeral head trial 3200*a*, 3200*b*, each additionally comprising a notch 3210, in-line with apertures 530, 540 and disposed along a portion of a perimeter of head trial 3200*a*, 3200*b*, are illustrated in FIG. 32.

Figure 29:
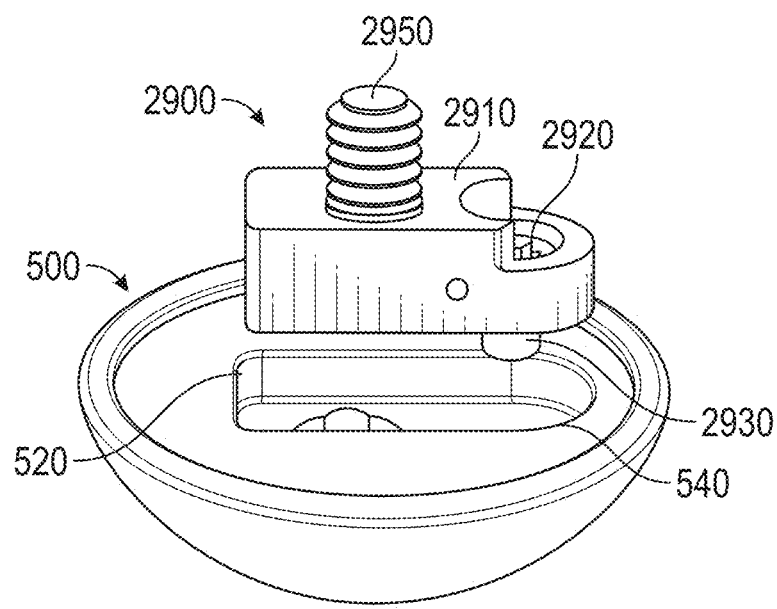
FIG. 29 illustrates a perspective view of a bottom of the humeral head trial of FIG. 28 and an adapter, in accordance with some example embodiments.
Figure 30:
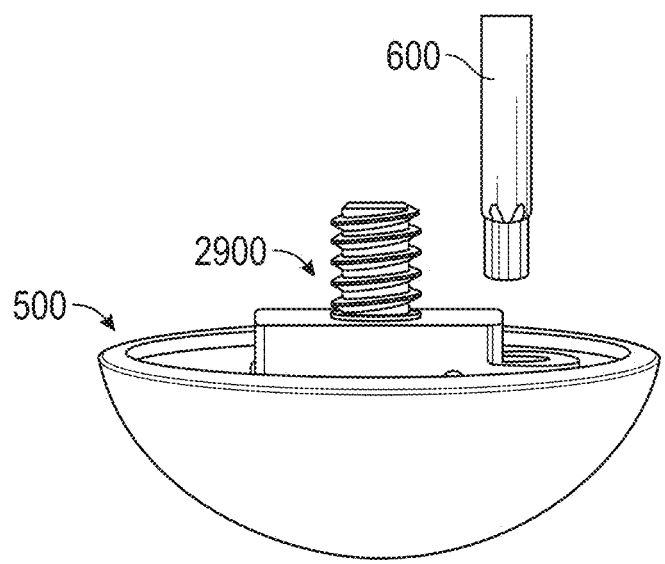
FIG. 30 illustrates a side view of an assembly of the humeral head trial and adapter of FIG. 28, in accordance with some example embodiments.

Once an appropriately sized head trial 500, 3200a, 3200b is selected, it may be trial fitted onto the proximal humerus 100. As illustrated by FIG. 29, a punch-head trial adapter 2900 may be inserted into recess 520 in bottom surface 510 of head trial 500, 3200a, 3200b. Punch-head trial adapter 2900 comprises a body 2910 having a shape and/or footprint that is complementary to the shape and/or footprint of recess 520 in bottom surface 510 of head trial 500, 3200a, 3200b. Adapter 2900 further comprises an aperture 2920 configured to receive a first screw 2930 and first screw 2930 is configured to mate with second aperture 540 of head trial 500, 3200a, 3200b and, thereby, couple adapter 2900 to head trial 500, 3200a, 3200b. In some embodiments, driver 600 may be utilized to tighten first screw 2950 (see, e.g., FIG. 30).

Figure 31:
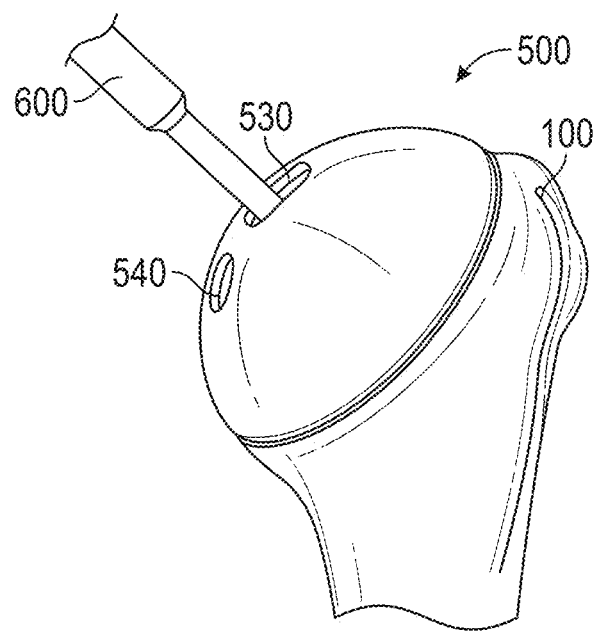
FIG. 31 illustrates a perspective view of the assembly of FIG. 30 coupled to the proximal humerus, in accordance with some example embodiments.

Adapter 2900 further comprises a second screw 2950 extending away from body 2910 and configured to mate with an aperture of punch 2000 (see, e.g., FIG. 20) while punch 2000 is disposed within proximal humerus 100. If humeral protector 2500 was used, protector 2500 may be disassembled from punch 2000, for example utilizing driver 600, before coupling humeral head trial 500, 3200a, 3200b to punch 2000. As illustrated in FIG. 31, humeral head trial 500, 3200a, 3200b may be coupled to punch 2000, for example by threading second screw 2950 into the aperture of punch 2000 (see, e.g., FIG. 20) utilizing driver 600. Care should be taken not to overtighten second screw 2950. At this point, coverage and height of humeral head trial 500 can be confirmed prior to reduction.

In some implementations, additional humeral head height may be desired. In some such implementations, a neutral humeral head trial 3300 and punch-head trial adapter 3400, e.g., of a Turon™ Modular Shoulder System, may also be compatible with systems for shoulder arthroplasty as described anywhere herein. For example, FIG. 33 illustrates humeral head trial 3300 and FIG. 34 illustrates punch-head trial adapter 3400.

If humeral protector 2500 was used, protector 2500 may be disassembled from punch 2000, for example utilizing driver 600, before coupling adapter 3400 to proximal humerus 100.

Figure 33:
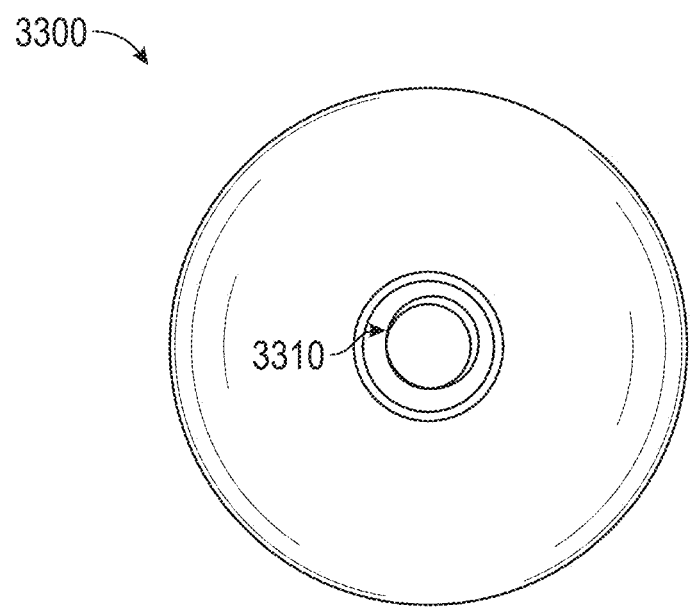
FIG. 33 illustrates a top view of yet another alternative humeral head trial, in accordance with some example embodiments.
Figure 34:
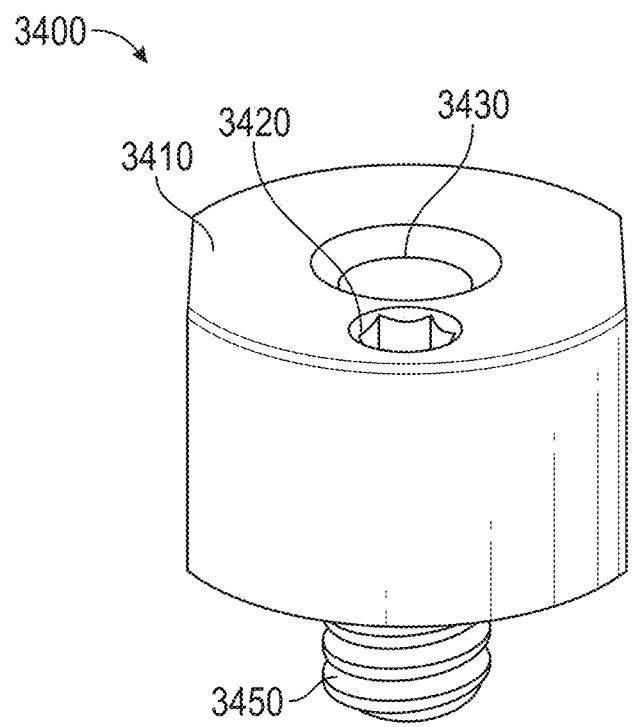
FIG. 34 illustrates an adapter for the humeral head trial of FIG. 33, in accordance with some example embodiments.

As illustrated by FIG. 33, humeral head trial 3300 comprises a central aperture 3310 configured to receive a screw for coupling humeral head trial 3300 to punch-head adapter 3400. As illustrated by FIG. 34, punch-head trial adapter 3400 comprises a body 3410 and body 3410 comprises a first aperture 2920 configured to receive a screw 3450 that is configured to mate with an aperture of punch 2000 (see, e.g., FIGS. 20 and 35). Adapter 3400 further comprises a second aperture 3430 configured to receive a screw that is configured to couple humeral head trial 3300 to adapter 3400, through central aperture 3310. In some embodiments, a driver 3500 (for example a 3.5 mm Hex driver) may be utilized to tighten first screw 3450 (see, e.g., FIG. 35).

Figure 35:
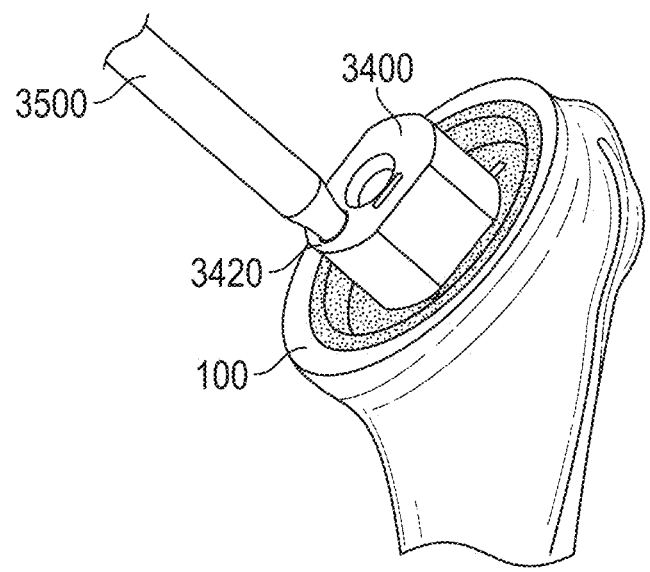
FIG. 35 illustrates the adapter of FIG. 34 coupled to the implanted punch of 24, in accordance with some example embodiments.
Figure 36:
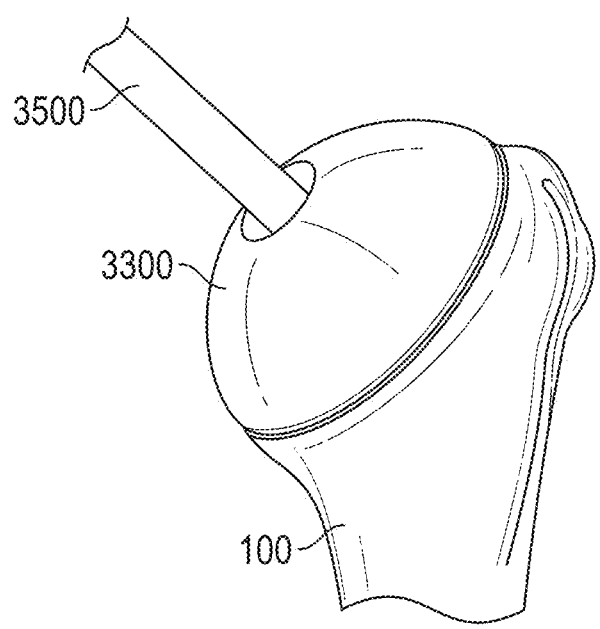
FIG. 36 illustrates the humeral head trial of FIG. 33 coupled to the adapter as in FIG. 35, in accordance with some example embodiments.

As illustrated in FIG. 35, adapter 3400 may be coupled to punch 2000, for example by threading screw 3450 into the aperture of punch 2000 (see, e.g., FIG. 20) utilizing driver 3500. Care should be taken not to overtighten screw 3450. Once adapter 3400 is coupled to punch 2000, humeral head trial 3300 may be secured to adapter 3400, for example utilizing driver 3500 to thread a screw through central aperture 3310 and into second aperture 3430. At this point, coverage and height of humeral head trial 3300 can be confirmed prior to reduction.

Trial Component Removal

Once humeral head trialing is complete, the trialing components may be removed from proximal humerus 100. For example, if humeral head trial 500, 3200a, 3200b was utilized (see at least, e.g., FIGS. 28-32), driver 600 may be utilized to remove the assembly of humeral head trial 500, 3200a, 3200b and adapter 2900. If humeral head trial 3300 was utilized (see at least, e.g., FIGS. 33-36), driver 3500 may be utilized to remove humeral head trial 3300 and then adapter 3400.

Figure 37:
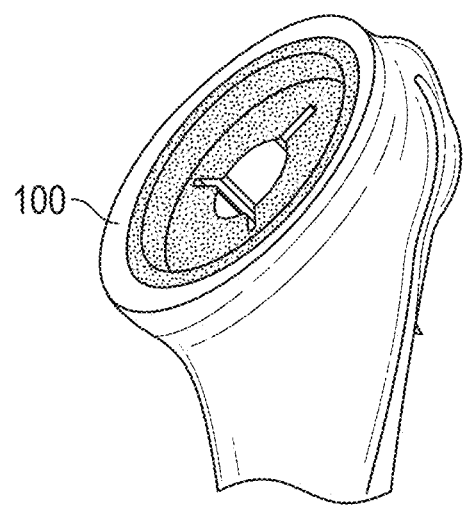
FIG. 37 illustrates the humeral head with the punch of FIG. 24 removed, in accordance with some example embodiments.

Punch inserter handle 2100 (see, e.g., FIG. 21) may then be coupled to punch 2000 and a mallet used to gently remove punch 2000 from proximal humerus 100. Where humeral head trial 500, 3200a, 3200b is utilized, a humeral head trial construct extractor (not shown) may be gently impacted to carefully remove the assembly of humeral head trial 500, 3200a, 3200b, adapter 3400 and punch 2000. FIG. 37 illustrates proximal humerus 100 with punch 2000 removed.

Humeral Head and Neck Implant Assembly

Figure 38:
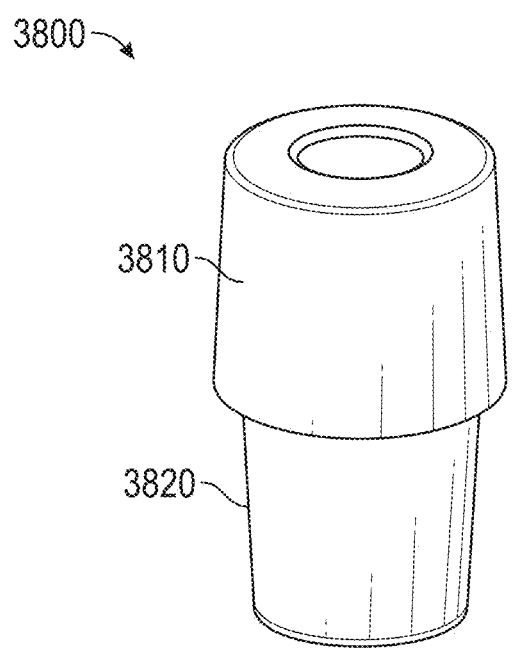
FIG. 38 illustrates a neck implant, in accordance with some example embodiments.
Figure 41:
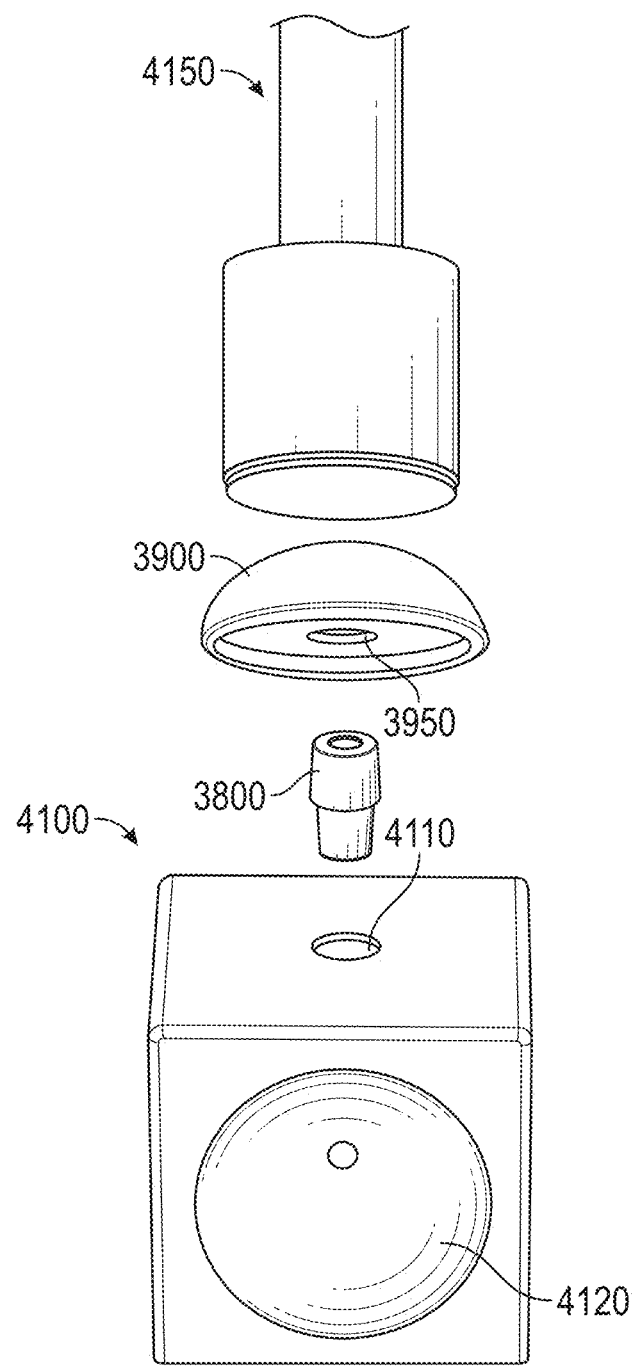
FIG. 41 illustrates a perspective view of a first procedure utilizing an impaction fixture for coupling a humeral head implant to the neck implant of FIG. 40, in accordance with some example embodiments.

As illustrated in at least FIGS. 39 and 40, an implant assembly for shoulder arthroplasty may comprise a cementless stem 5300, which is coupled or couplable to a neck implant 3800, which is coupled or couplable to a humeral head 3900, which is configured to articulate against one or both of a glenoid socket or a glenoid implant 4000 of a patient. As can be seen in FIG. 38, neck implant 3800 includes a first tapered end 3810 and a second tapered end 3820 that is smaller in diameter than the first tapered end. First and second tapered ends 3810, 3820 may meet one another substantially halfway through the length of extent of neck implant 3800 and may both be shaped substantially as a portion of a cone or of a cylinder that tapers toward each end.

As can be seen in FIG. 39, humeral head 3900 comprises a substantially flat bottom side 3910 and a central aperture 3950 extending into humeral head from bottom side 3910. In some embodiments, sidewalls of aperture 3950 are tapered, for example Morse tapered, and are configured to receive and couple with first tapered end 3810 of neck implant 3800.

Two general methods are provided for assembling the humeral head implant and the humeral neck implant, each utilizing an impaction fixture 4100. A first method, a "neck-first" approach illustrated by FIG. 41, utilizes a neck recess 4110 in impaction fixture 4100. For example, second tapered end 3820 of neck implant 3800 is inserted into neck recess 4110 such that first end 3810 is facing up. Humeral head 3900 is placed onto neck implant 3800, such that first end 3810 of neck implant 3800 is disposed in central aperture 3950 of humeral head 3900, and then pressed down to initiate the Morse taper between central aperture 3950 and first end 3810. A humeral head impactor 4150 may then be placed on humeral head 3900 and tapped with a mallet to properly seat first end 3810 in central aperture 3950.

Figure 42:
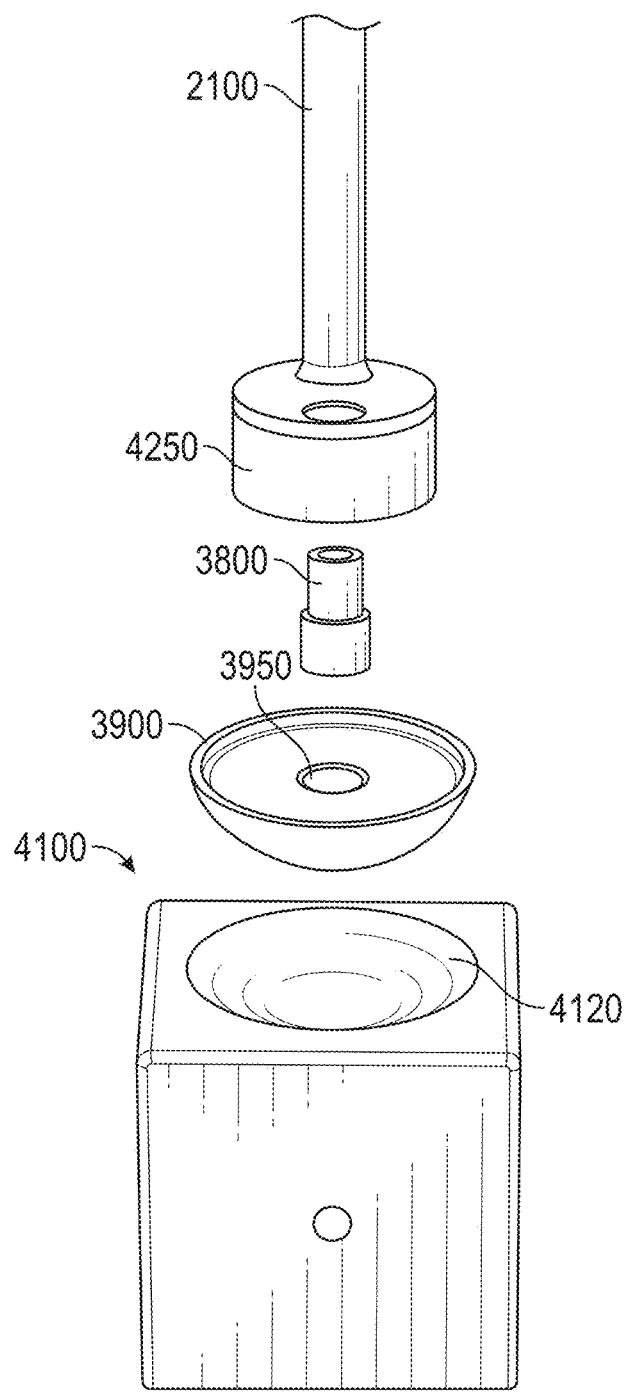
FIG. 42 illustrates a perspective view of a second procedure utilizing an impaction fixture for coupling a humeral head implant to the neck implant of FIG. 40, in accordance with some example embodiments.
Figure 45:
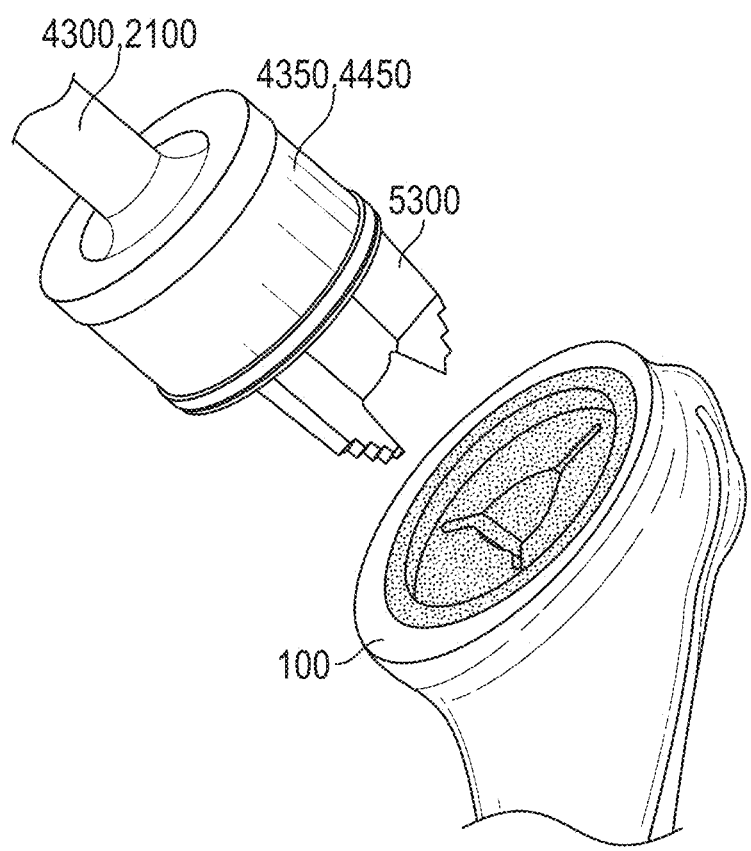
FIG. 45 illustrates a perspective view of impaction of a humeral stem into the prepared proximal humerus according to the stem-insertion approaches of FIGS. 43 and 44, in accordance with some example embodiments.

A second method, a "head-first" approach illustrated by FIG. 42, utilizes one or more humeral head recesses 4120 in impaction fixture 4100. For example, humeral head 3900 is placed in the appropriately sized humeral head recess 4120 in impaction fixture 4100. In some embodiments, fixture impaction 4100 comprises a concavity on each of two sides, for example one engraved with "38 mm-42 mm" and the other engraved with "46 mm-56 mm". First end 3810 of neck implant 3800 may be disposed into central aperture 3950 of humeral head 3900 and pressed down into humeral head 3900 to initiate the Morse taper between central aperture 3950 and first end 3810. A neck impactor 4250 can be assembled to punch inserter handle 2100 (see, e.g., FIG. 21) and positioned over neck implant 3800. While cupping the humeral implants and neck impactor 4250, tap handle 2100 with a mallet to properly seat first end 3810 in central aperture 3950.

In Situ Implant Assembly—Stem Insertion Approaches

In some systems and/or kits for shoulder arthroplasty as described anywhere herein, instrumentation for two stem-insertion approaches are provided—one threaded and the other non-threaded.

Instrumentation for a threaded approach is illustrated in FIG. 43, where a stem inserter handle 4300 comprises a threaded tip 4350 configured to directly mate with a humeral stem 5300 of a desired size. In some embodiments, threaded tip 4350 can comprise one or both of metal and/or plastic. Upon assembly of humeral stem 5300 to inserter handle 4300, stem 5300 can be placed on or into the prepared surgical site of proximal humerus 100. At least one advantage of utilizing a threaded approach is reduced mishandling and/or dropping of stem 5300, by virtue of stem 5300 being physically engaged with threaded tip 4350 of handle 4300.

Instrumentation for a non-threaded approach is illustrated in FIG. 44, where a non-threaded stem impactor 4450 is coupled to humeral punch inserter handle 2100. In some embodiments, non-threaded stem impactor 4450 can comprise one or both of metal and/or plastic. Upon assembly, stem 5300 can be placed into the prepared surgical site of proximal humerus 100. Since humeral stem 5300 is not physically engaged with non-threaded stem impactor 4450, caution should be taken not to drop stem 5300 when handling and/or passing the non-threaded stem impactor 4450/handle 2100 assembly. At least one advantage of the non-threaded approach is that non-threaded stem impactor 4450 may also be utilized as a tamp for impaction along a surface of a collar (see, e.g., FIG. 53) of stem 5300, not just at a female taper at a center of stem 5300. Another is allowance for quick assessments of stem insertion progress by virtue of the easy removal of the non-threaded stem impactor 4450/handle 2100 assembly from the non-physically engaged stem 5300 for full visibility of stem 5300 within the osteotomy. Yet another advantage is the inherent physical and/or spatial flexibility afforded by stem 5300 not being physically engaged with non-threaded impactor 4450.

Figure 46:
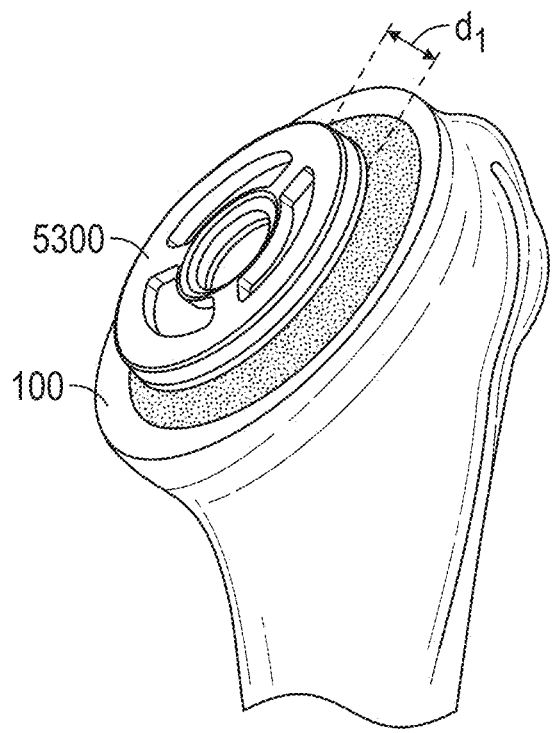
FIG. 46 illustrates a perspective view of the impacted humeral stem of FIG. 45, in accordance with some example embodiments.

Once humeral stem 5300 is properly aligned with the prepared site of proximal humerus 100 utilizing either of the above-described threaded or the non-threaded approaches (see, e.g., FIG. 45), and ensuring one implant fin is aligned superolaterally, the appropriate inserter handle assembly is tapped with a mallet until a collar of stem 5300 is proud of the osteotomy by a predetermined distance di, e.g., 3-5 mm, (see, e.g., FIG. 46). However, depending on subscapularis repair technique, it may be desirable to place sutures before final implantation of stem 5300.

Figure 47:
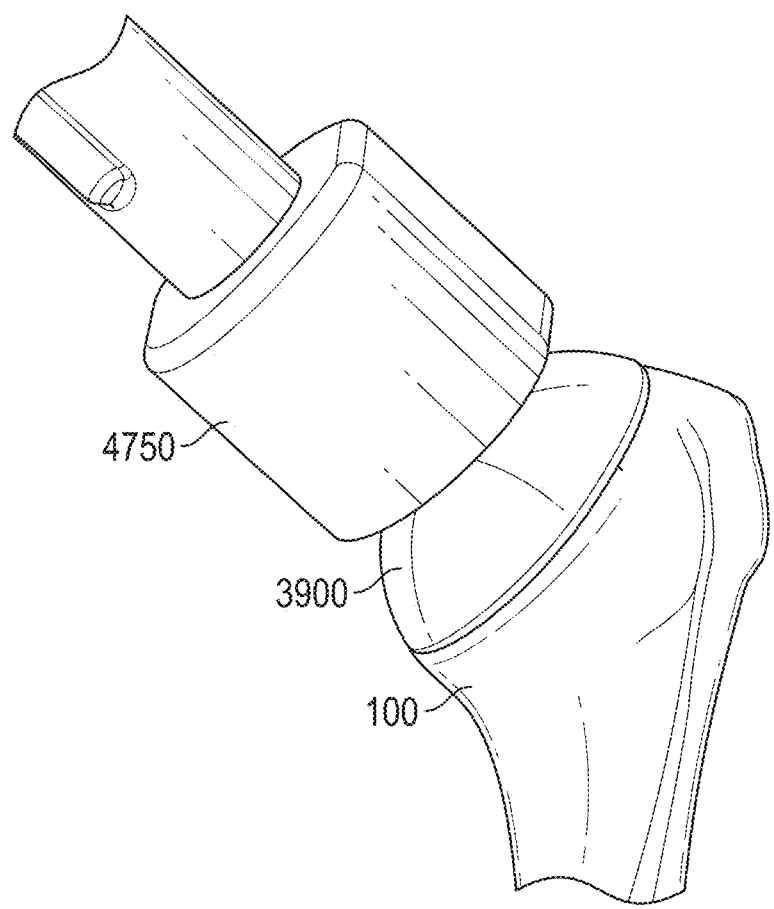
FIG. 47 illustrates a perspective view of instrumentation for installing a humeral head onto the impacted humeral stem of FIG. 46, in accordance with some example embodiments.

A humeral head impactor 4750 can be assembled, the assembly of humeral head 3900 and neck implant 3800 inserted into stem 5300, and impactor 4750 used to impact the assembly until humeral head 3900 is fully engaged and seated against proximal humerus 100, as illustrated for example, in FIG. 47. In some embodiments humeral head impactor 4750 can comprise one or both of metal and/or plastic.

Humeral Head Trialing After Stem Implantation

In some cases, it may be desirable to change humoral head 3900 size after implantation of stem 5300 has been completed. In some such cases, humeral head trials 500, 3200a, 3200b, 3300 may also be compatible with implanted humeral stem 5300 by utilizing a stem-head trial adapter between stem 5300 and humeral head trials 500, 3200a, 3200b, 3300, for example, as described and illustrated in connection with at least FIGS. 48 and 49. As previously described in connection with adapters 2900 and 3400, care should be taken not to overtighten the head trial assembly or stem-head trial adapter to stem 5300.

Figure 48:
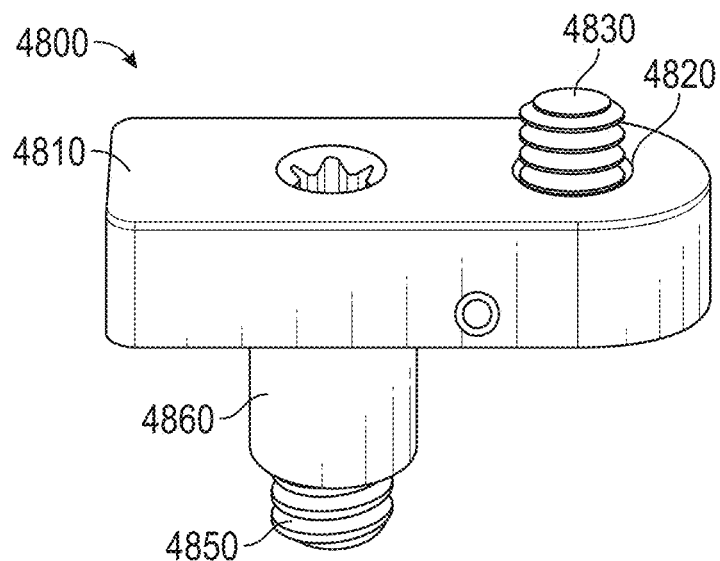
FIG. 48 illustrates a perspective view of an adapter for humeral head trialing utilizing the impacted humeral stem of FIG. 46, in accordance with some example embodiments.

For example, stem-head trial adapter 4800 illustrated in FIG. 48 may have construction substantially similar to that of adapter 2900 illustrated and described in connection with FIG. 29. Adapter 4800 may comprise a body 4810, an aperture 4820, a first screw 4830, and a second screw 4850 substantially corresponding to body 2910, an aperture 2920, a first screw 2930, and a second screw 2950, respectively, except that a spacer portion 4860 is disposed between body 4810 and second screw 4850.

Figure 49:
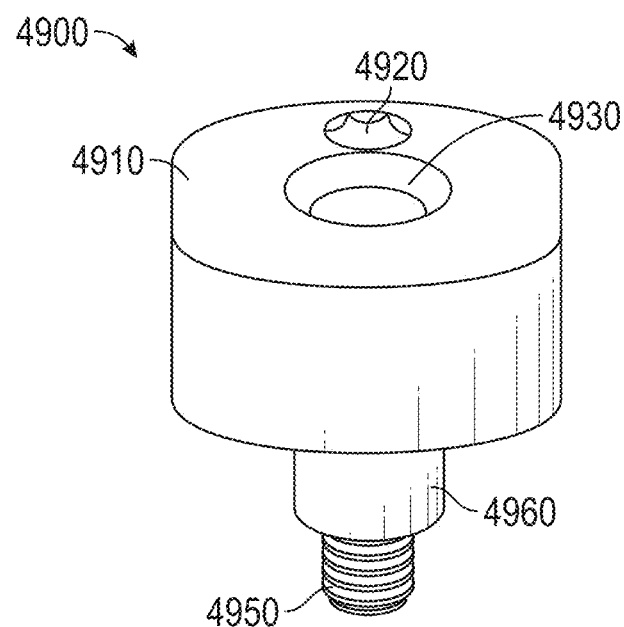
FIG. 49 illustrates a perspective view of another adapter for humeral head trialing utilizing the impacted humeral stem of FIG. 46, in accordance with some example embodiments.

Similarly, stem-head trial adapter 4900 illustrated in FIG. 49 may have construction substantially similar to that of adapter 3400 illustrated and described in connection with FIG. 34. Adapter 4900 may comprise a body 4910, a first aperture 4920, a second aperture 4930 and a screw 4950 substantially corresponding to body 3410, first aperture 3420, second aperture 3430 and first 3450, respectively, except that a spacer portion 4960 is disposed between body 4910 and screw 4950.

Upon confirmation and selection of a new humeral head 3900 size, adapter 4800 or 4900 and humeral head trials 500, 3200a, 3200b, 3300 may be removed from stem 5300 and implantation of the new humeral head 3900 may be affected as previously described. In some cases, additional bony or soft tissue preparation may be desirable to ensure engagement of the assembled humeral head 3900, neck implant 3800, implanted stem 5300 construct. Accordingly, it may be desirable to verify that this construct is properly and fully seated and engaged after impaction.

Stem Revision

Figure 50:
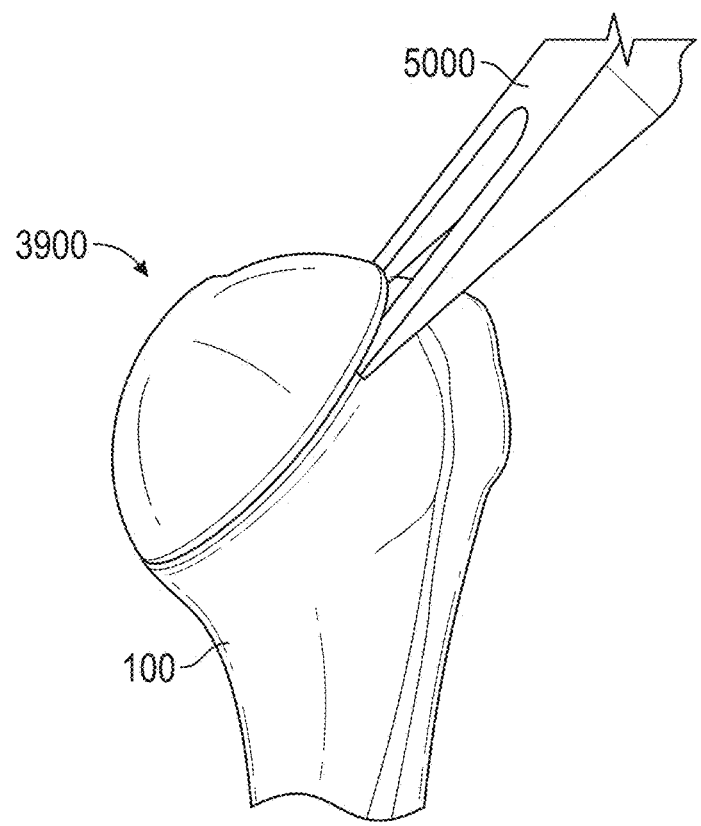
FIG. 50 illustrates a perspective view of instrumentation for humeral head revision, in accordance with some example embodiments.

In some cases, it may be desirable to perform a stem revision, in which stem 5300 is removed. In some such cases, removal of humoral head 3900 and neck implant 3800 can be achieved without disturbing a well-fixed stem 5300. For example, as illustrated in FIG. 50, humeral head 3900 may be removed using a head distractor 5000 comprising, for example, two prongs. The two prongs of head distractor 5000 may be placed between humeral head 3900 and the osteotomy surface and then distractor 5000 may be gently tapped with a mallet until the Morse taper with neck implant 3800 is disengaged.

Figure 51:
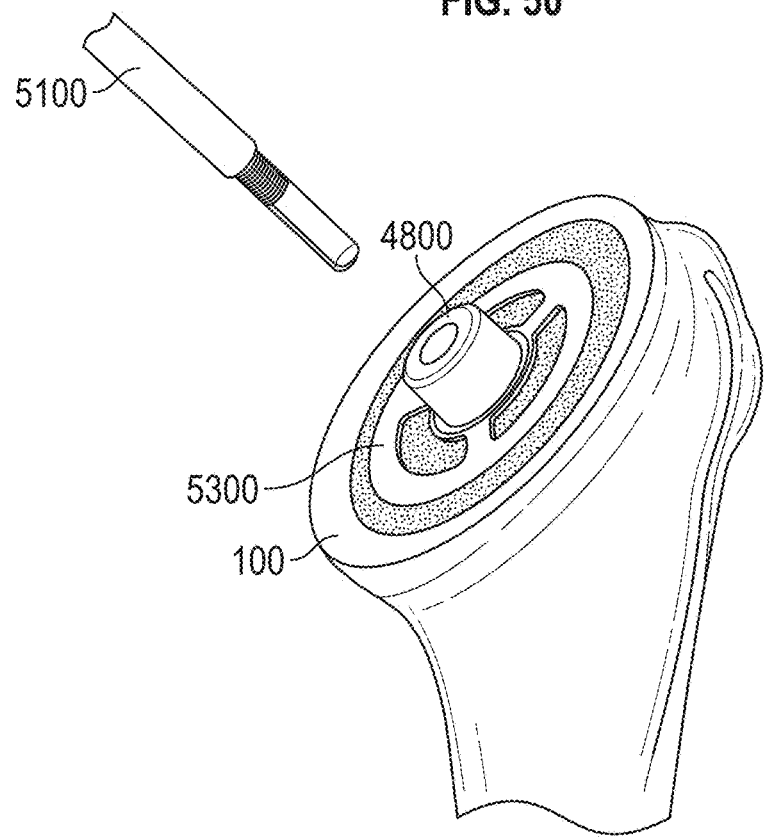
FIG. 51 illustrates a perspective view of additional instrumentation for humeral head revision, in accordance with some example embodiments.

As illustrated in FIG. 51, neck implant 3800 may be removed using a humeral neck extractor 5100 by, for example, attaching extractor 5100 to a ratchetting handle and threading a tip of the extractor 5100 into the threaded hole of neck implant 3800 until the tip bottoms out against stem 5300 and disengages the Morse taper.

Figure 52:
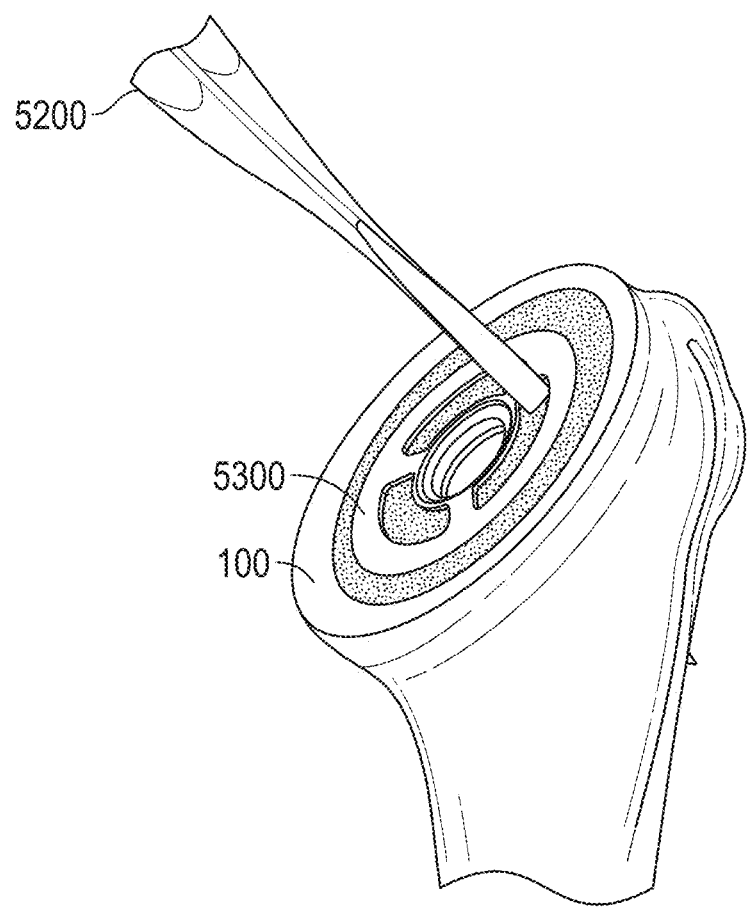
FIG. 52 illustrates a perspective view of further additional instrumentation for humeral head revision, in accordance with some example embodiments.

As illustrated in FIG. 52, an explantation tool 5200 and threaded stem inserter handle 4300 with threaded tip 4350 can be utilized to remove stem 5300. For example, explantation tool 5200 can be utilized through and around the collar windows of stem 5300 to access regions of bone ingrowth, including along the fins and collar. Explantation tool 5200 may be gently tapped with a mallet to break the regions of bony ingrowth. Threaded tip 4350 of stem inserter handle 4300 can then be coupled to stem 5300 and stem 5300 gently tapped out from proximal humerus 100 until stem 5300 is sufficiently clear from the osteotomy surface. In some embodiments, twisting stem inserter handle 4300 when coupled to stem 5300 can caid in further loosening stem 5300 to facilitate the removal process.

Aspects of the Cementless Humeral Stem

Several aspects of cementless humeral stem 5300 will now be described in connection with at least FIGS. 53-61. Humeral stem 5300 comprises a collar 5310. In some embodiments, collar 5310 has a substantially circular shape.

As illustrated, collar 5310 comprises one or more windows 5320 configured to provide visual and physical access to the space under collar 5310 (e.g., bone in-growth surfaces once implanted) therethrough, facilitating the performance of revision surgeries. In some embodiments, windows 5320, together, have a substantially circular shape interrupted by portions of collar 5310 coupling an outer ring of collar 5310 with a central portion of collar 5310.

Humeral stem 5300 further comprises a central body 5340 extending from a bottom side of collar 5310. In some embodiments, central body 5340 has a substantially cylindrical shape. In some embodiments, central body 5340 may taper slightly along its length of extension away from the bottom side of collar 5310.

Humeral stem 5300 further comprises a plurality of fins 5350 (e.g., 3 are shown, though any number are contemplated) extending away from the bottom side of collar 5310 and extending radially away from central body 5340. Once implanted, fins 5350 provide rotational stability to stem 5300.

In some embodiments, each of fins 5350 may comprise side edges 5375, that may taper inward slightly as the fin extends downward.

Figure 53:
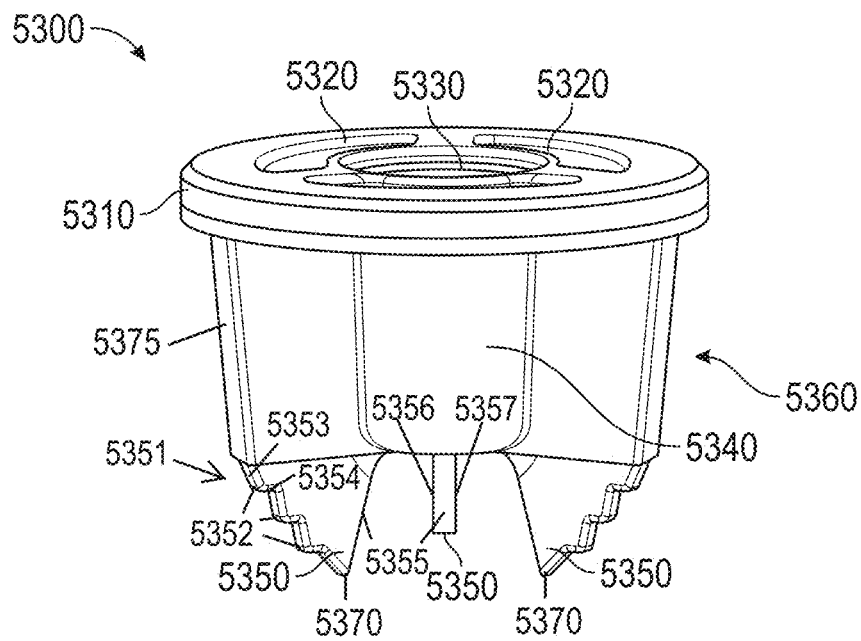
FIG. 53 illustrates a perspective side view of a humeral stem, in accordance with some example embodiments.
Figure 54:
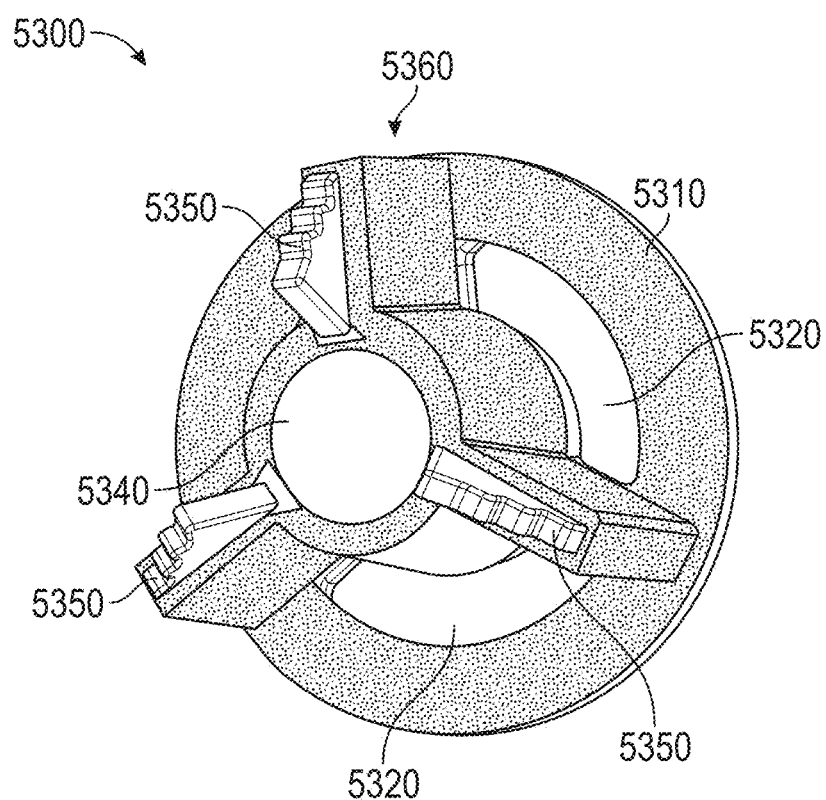
FIG. 54 illustrates a perspective bottom view of the humeral stem of FIG. 53, in accordance with some example embodiments.
Figure 55:
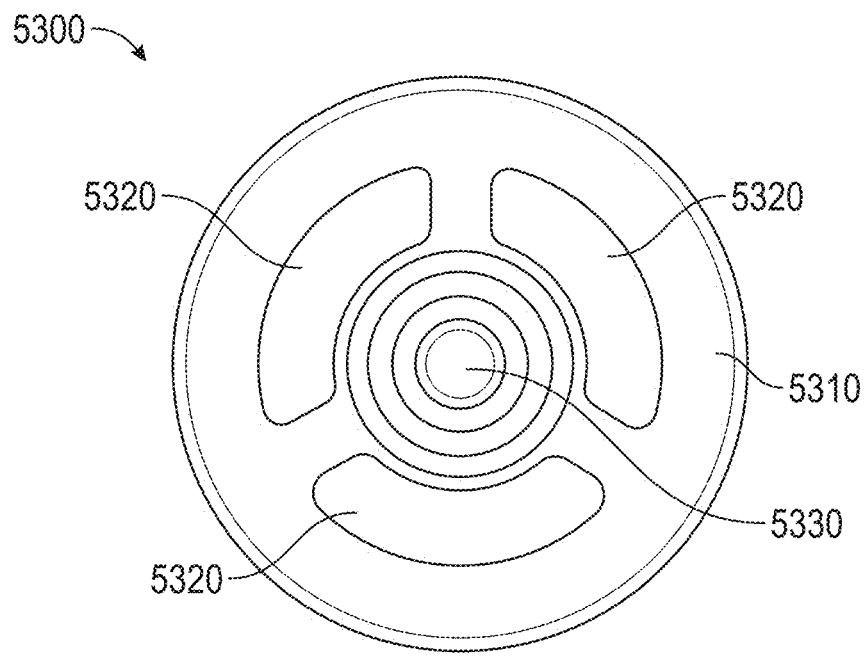
FIG. 55 illustrates a top view of the humeral stem of FIG. 53, in accordance with some example embodiments.
Figure 56:
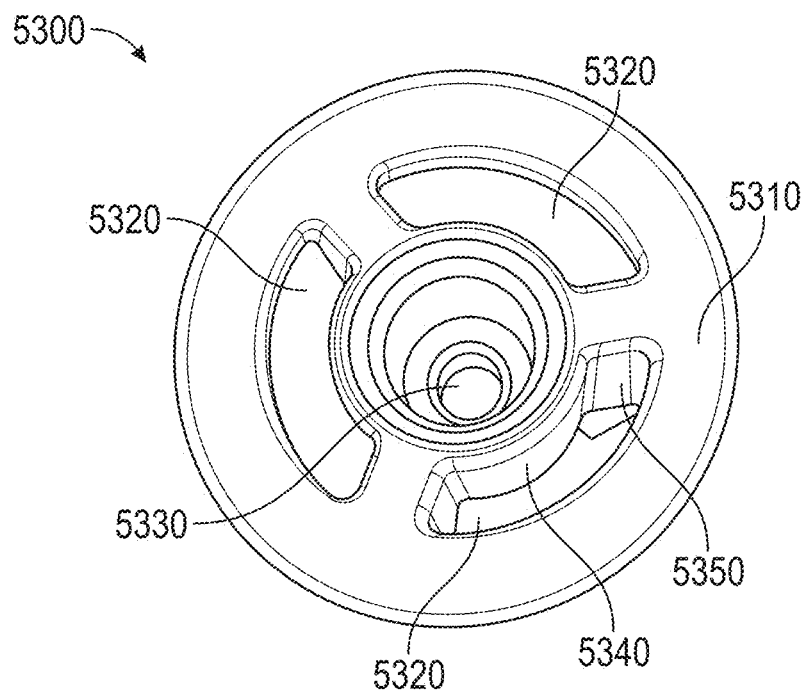
FIG. 56 illustrates a perspective top view of the humeral stem of FIG. 53, in accordance with some example embodiments.

Each fin may also have two generally downwardly facing edges denoted 5351 and 5355 in FIG. 53, and which may be referred to herein as fin bottom edges. Bottom edge 5355, referred to herein as an inner bottom edge or medial edge, extends downward from the central body and away from the central axis of the stem to a lowermost tip of the fin 5370. The outwardly directed slope of the inner bottom edge 5351 as it extends away from the central body can reduce the amount of bone removed from the humeral canal during the surgery. However, inner bottom edges that extend straight downward or even inward from the central body may be utilized in some embodiments.

The other bottom edge 5351, referred to herein as an outer bottom edge, extends downward and toward the central axis of the stem where it meets the inner bottom edge at the lowermost tip of the fin 5370.

In some embodiments, the outer bottom edge 5351 may comprise a stepped or serrated edge. For example, as shown in FIG. 53, outer bottom edge 5351 may comprise one or more teeth or steps 5352. In some embodiments, each tooth/step 5352 may comprise a substantially outward-facing surface 5353 and a substantially downward-facing surface 5354 meeting one another to define a tip of the respective tooth 5352. In the embodiment shown in FIG. 53, surfaces 5354 are oriented essentially perpendicular to the central axis to face essentially directly downward. The surfaces 5353 are angled to face in an oblique direction partially downward and partially outward. The orientation of the surfaces 5354 and 5352 may vary for different fins or different teeth on a fin. In the embodiment of FIG. 53, for example, the outward facing surfaces 5353 at the bottom of the fins are more downwardly oriented more than the outward facing surfaces 5353 where the serrated edges meet the side edges 5375. The tips of the teeth 5352 may lie on a straight line or a curve. The tips of the teeth may lie on a curve that is outwardly convex. The tips of the teeth may also lie on a curve that is outwardly concave. In some embodiments, some fins may not be serrated. In some embodiments, one or more of the inner bottom edges 5355 may be serrated in addition to or alternatively to serrations on the outer bottom edge.

In some embodiments, each of fins 5350 may comprise a first side wall 5356 and a second side wall 5357. In some embodiments, side walls 5356, 5357 may be substantially parallel to one another such that each fin 5350 has a substantially uniform thickness as measured by a separation between sidewalls 5356, 5357. In some embodiments, one or both of edge 5351 and edge 5355 may comprise surfaces that are substantially orthogonal to first and second sidewalls 5356, 5357. In some embodiments surfaces 5353 and surfaces 5354 meet first and second sidewalls 5356, 5357 to form beveled, or slightly rounded, transitions.

In some embodiments, the inner bottom edge 5355 of one or more of fins 5350 extends radially, further away from an axial or longitudinal centerline of stem 5300 along a distal length of extension of fins 5350 to the bottom tip 5370. In other words, a radial distance between edge 5355 of one or more of fins 5350 and a centerline of stem 5300 and/or of central body 5340 of stem 5300 increases along a distal length of extension of fin(s) 5350. In some embodiments, this tapering feature functions to focus the force, imparted to stem 5300 during impaction, to a smaller surface area at a distal end of the one or more fins 5350 (e.g., outer bottom edge 5351 and teeth/steps 5352), thereby improving the cutting, compacting and/or impacting function(s) of stem 5300. In some embodiments, this tapering feature may additionally or alternatively cause edges 5355 of fins 5350 to increase compaction of bone that is in contact with edges 5355 of fins 5350 toward the centerline of stem 5300.

In some embodiments, at least a portion of fins 5350 extends below central body 5340. The serrated edges (e.g., the teeth/steps 5352 of outer bottom edge 5351) provide additional cutting features and ensure adequate press-fit of fins 5350 and/or a porous coating 5360 of stem 5300 in the weaker bone located deeper into the metaphysis.

In some embodiments, serrated outer bottom edges 5351 of fins 5350 taper toward a central axis of stem 5300 along a distal length of extension of fins 5350. In other words, a radial distance between serrated outer/bottom edges 5351 of fins 5350 and a centerline of stem 5300 and/or of central body 5340 of stem 5300 decreases along a distal length of extension of the outer bottom edges 5351 of fin(s) 5350. For example, as will be described in more detail in connection with FIGS. 57 and 58 below, upon initial impaction of stem 5300 into the prepared site of proximal humerus 100, serrated bottom/outside edges 5351 fins 5350 both cut and compact bone of a medial portion of the metaphysis of humerus 100 toward relatively denser cancellous bone of a peripheral portion of humerus 100 when press-fit therein, thereby providing sufficient press-fitting for cementless fixation of humeral stem 5300 into humerus 100. Specifically, for a given fin 5350 of stem 5300, substantially outward-facing surfaces 5353 of teeth/steps 5352 may compact bone of a medial portion of the metaphysis of humerus 100 toward relatively denser cancellous bone 5710 of a peripheral portion of humerus 100. For such a given fin 5350 of stem 5300, substantially downward-facing surfaces 5354 of teeth/steps 5352 may additionally compact bone in a substantially downward direction. A shearing force between the above-described compacted bone and immediately adjacent portions of the bone may also cause fins 5350 (e.g., at least teeth/steps 5352 of serrated bottom/outside edge 5351) to cut into the bone.

In addition, fins 5350 extending farther distally than central body 5340 reduces an amount of bone removal in the canal of the humerus. Accordingly, this feature is canal-sparing and allows for metaphyseal placement of stem 5300 that avoids the humeral canal morphology. Fins 5350 are illustrated as being equally spaced about central body 5340 from one another, though any relative spacing and orientations between fins 5350 are also contemplated.

Stem 5300 may further comprise a porous coating 5360 disposed on at least an underside of collar 5310, on fins 5350 and on central body 5340. Porous coating 5360 may have variability in pore sizes, similar to a "lava rock" type of structure, configured to aid in the apposition of bone for excellent in-growth results. Since, as previously described, stem 5300 is implanted utilizing instrumentation that is line to line with the substrate, substantially all of porous coating 5360 has the potential to be press-fit. Accordingly, stem 5300 is configured for exceptional cementless (e.g., press-fit) fixation within the humerus.

Figure 60:
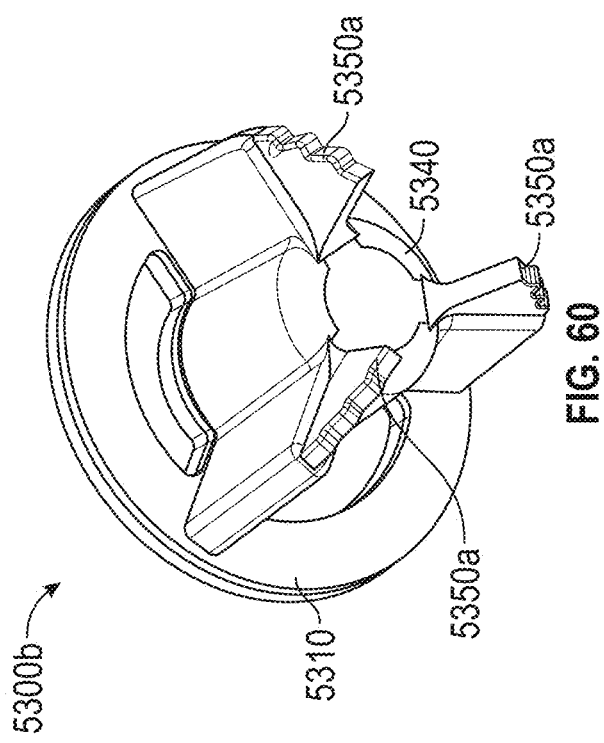
FIG. 60 illustrates a perspective bottom view of a medium-sized version of the humeral stem of FIG. 53, in accordance with some example embodiments.
Figure 61:
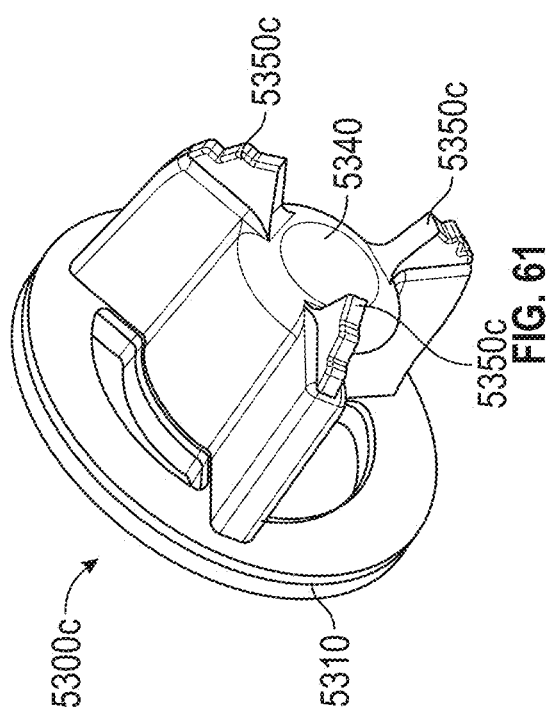
FIG. 61 illustrates a perspective bottom view of a small-sized version of the humeral stem of FIG. 53, in accordance with some example embodiments.
Figure 59:
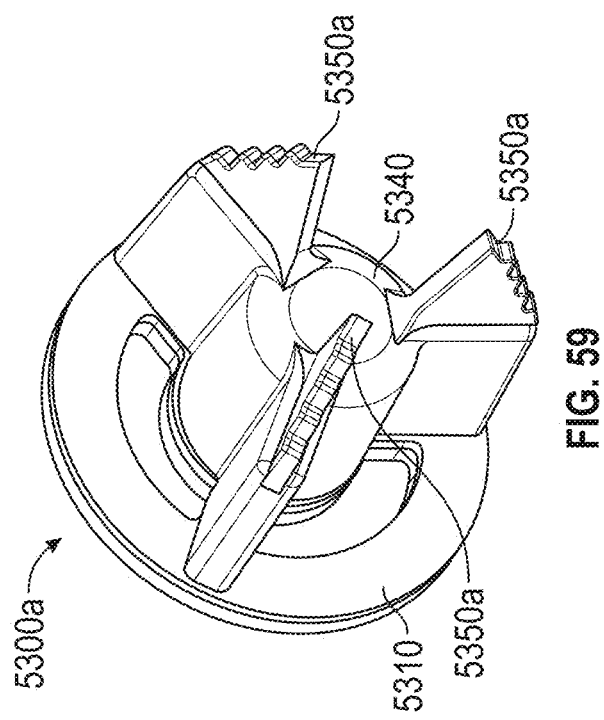
FIG. 59 illustrates a perspective bottom view of a large-sized version of the humeral stem of FIG. 53, in accordance with some example embodiments.
Figure 69:
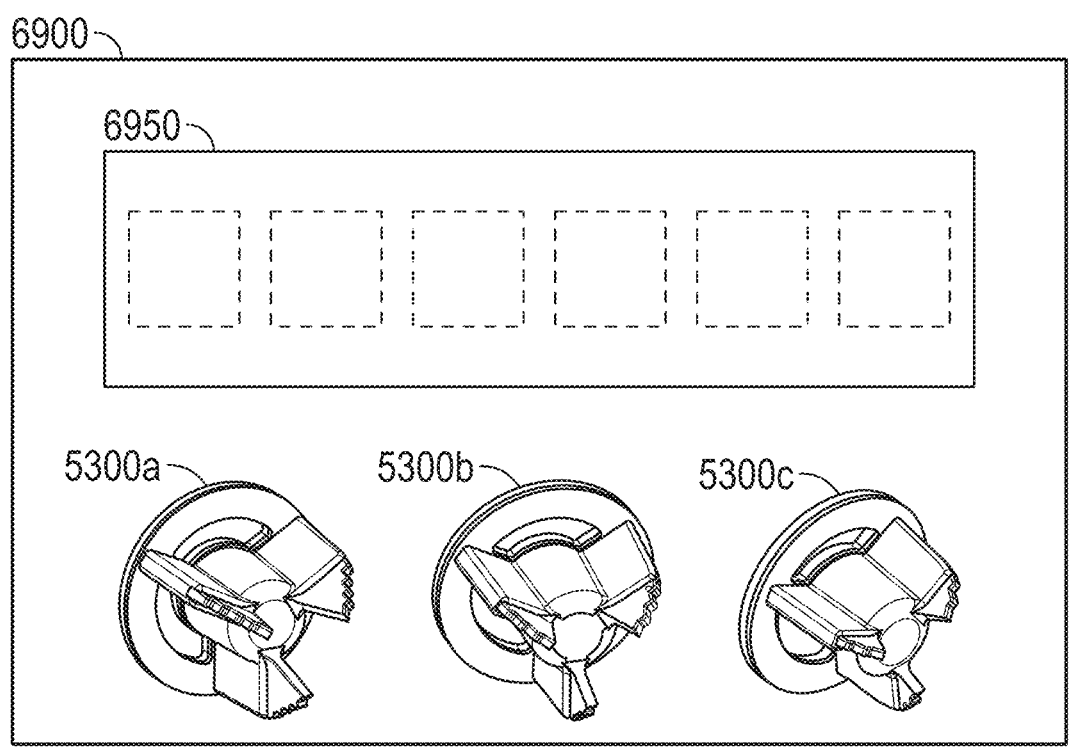
FIG. 69 illustrates a surgical kit for shoulder arthroplasty, in accordance with some example embodiments.

As described above, stem 5300 may be provided in several different sizes. For example, as illustrated by FIGS. 59-61, a large stem 5300a, a medium stem 5300b and a small stem 5300c may each be provided in a system and/or kit for shoulder arthroplasty as described anywhere herein. For example, an example of such a surgical kit 6900 is illustrated in FIG. 69, comprising plurality of stems 5300a-c. A kit, such as kit 6900, may comprise one or more implant components, tools and/or instruments as described anywhere in this disclosure and, in some embodiments, may be provided together for the purpose of performing a shoulder arthroplasty, for example as described anywhere in this disclosure. Accordingly, in some embodiments, kit 6900 may further comprise any one or more additional implant or implant system components, instruments or tools 6950 as described anywhere in this disclosure.

In some embodiments, collar 5310 of each of stems 5300a-c may have a same or consistent size for inter-compatibility. In some embodiments, central body 5340 of each of stems 5300a-c may also have a same or consistent size. However, plurality of fins 5350a, 5350b and 5350c may each have a different size. For example, fins 5350a of large stem 5300 may extend farther radially, away from central body 5340 and/or farther toward a perimeter of collar 5310 compared to either of fins 5350b of medium stem 5300b or fins 5350c of small stem 5300c. Similarly, fins 5350b of medium stem 5300 may extend farther radially, away from central body 5340 and/or farther toward a perimeter of collar 5310 compared to fins 5350c of small stem 5300c.

In addition, or alternative, fins 5350a of large stem 5300a may extend farther distally beyond central body 5340 compared to either of fins 5350b of medium stem 5300b or fins 5350c of small stem 5300c. Similarly, fins 5350b of medium stem 5300 may extend farther distally beyond central body 5340 compared to fins 5350c of small stem 5300c.

In yet further addition, or yet further, alternative fins 5350a of large stem 5300a may have a greater number of teeth/steps 5352 (see, e.g., FIG. 53) compared to either of fins 5350b of medium stem 5300b or fins 5350c of small stem 5300c. Similarly, fins 5350b of medium stem 5300 may have a greater number of serrated teeth/steps 5352 compared to fins 5350c of small stem 5300c.

In yet further addition, or yet further alternative, a first angle between a medial edge and the outer or bottom serrated edge of fins 5350a of large stem 5300 is smaller than a second angle between a medial edge and the outer or bottom serrated edge of fins 5350b of medium stem 5300b and smaller than a third angle between a medial edge and the outer or bottom serrated edge of fins 5350c of small stem 5300c. Similarly, the second angle between the medial edge and the outer or bottom serrated edge of fins 5350b of medium stem 5300b is smaller than the third angle between a medial edge and the outer or bottom serrated edge of fins 5350c of small stem 5300c.

Figure 57:
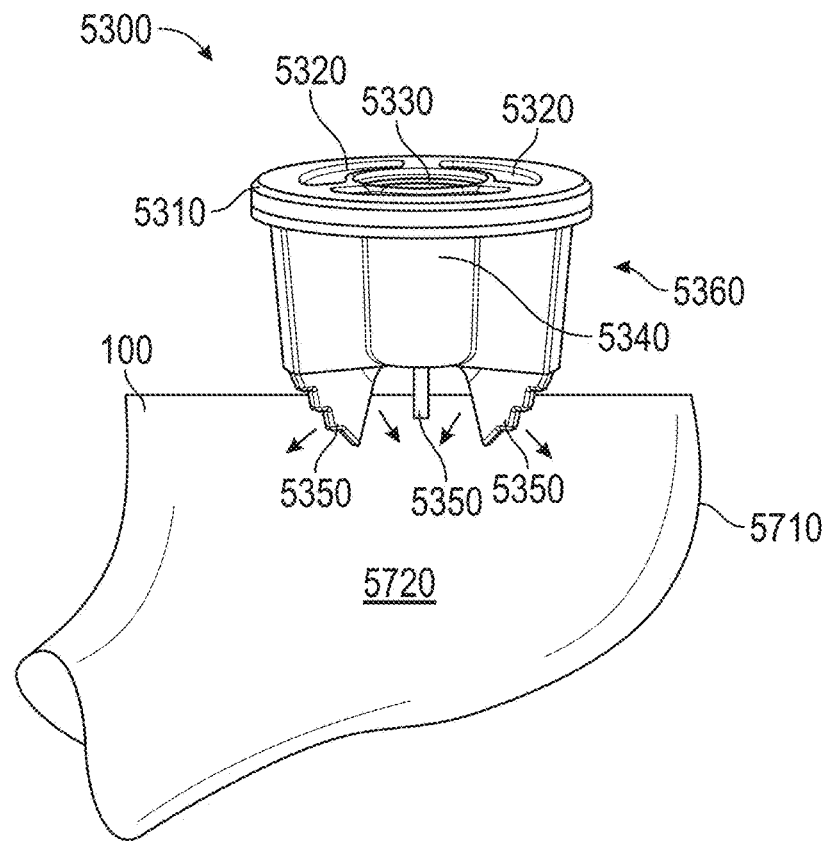
FIG. 57 illustrates a perspective side view of the humeral stem of FIG. 53 upon initial impaction into the prepared proximal humerus, in accordance with some example embodiments.
Figure 58:
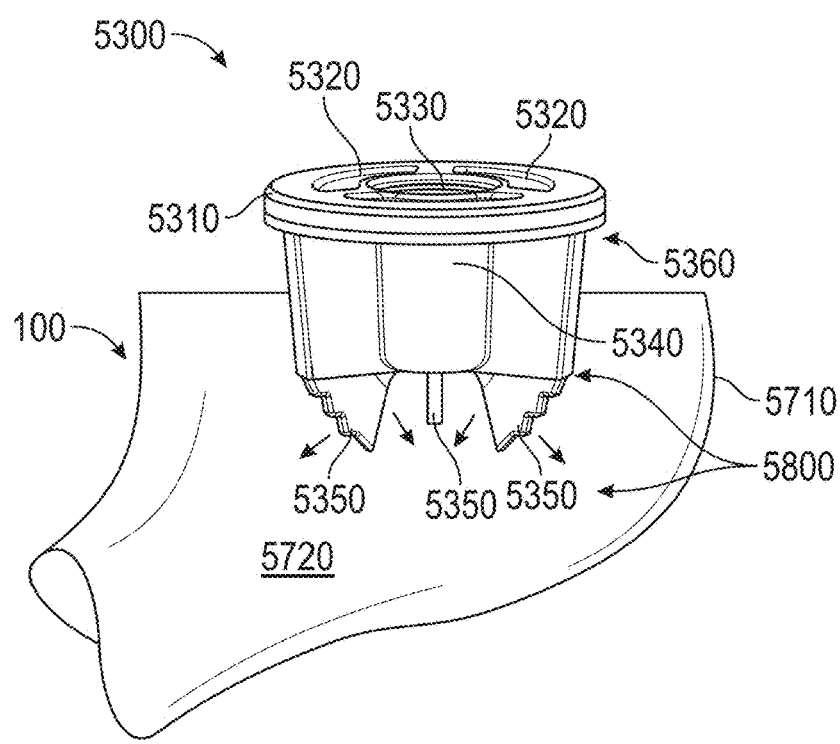
FIG. 58 illustrates a perspective side view of the humeral stem of FIG. 53 mid-impaction into the prepared proximal humerus, in accordance with some example embodiments.

As illustrated in FIGS. 57 and 58, proximal humerus 100 comprises an outer layer of cortical bone 5710 and a region of cancellous bone 5720 within this outer layer. Upon initial impaction of stem 5300 into the prepared site of proximal humerus 100, fins 5350, especially serrated bottom/outside edges 5351, both cut and compact bone of a medial portion of the metaphysis of humerus 100 toward relatively denser cancellous bone 5720 of a peripheral portion of humerus 100 when press-fit therein, thereby providing sufficient press-fitting for cementless fixation of humeral stem 5300 into humerus 100. For example, the inner/medial edges 5355 may cut into and compact bone toward an axial centerline of stem 5300a. In further or alternative example, the serrated outer/bottom edges 5351 may cut into and compact a medial portion of the metaphysis of humerus 100 toward relatively denser cancellous bone 5720 of a peripheral portion of humerus 100. In this way, implanting of stem 5300 simultaneously and artificially increases the density, strength and stability of the bone surrounding stem 5300.

Example Method(s) of Use

The disclosure now turns to one or more example methods of implanting a humeral implant in a humerus of a patient, as described anywhere in this disclosure.

Figure 67:
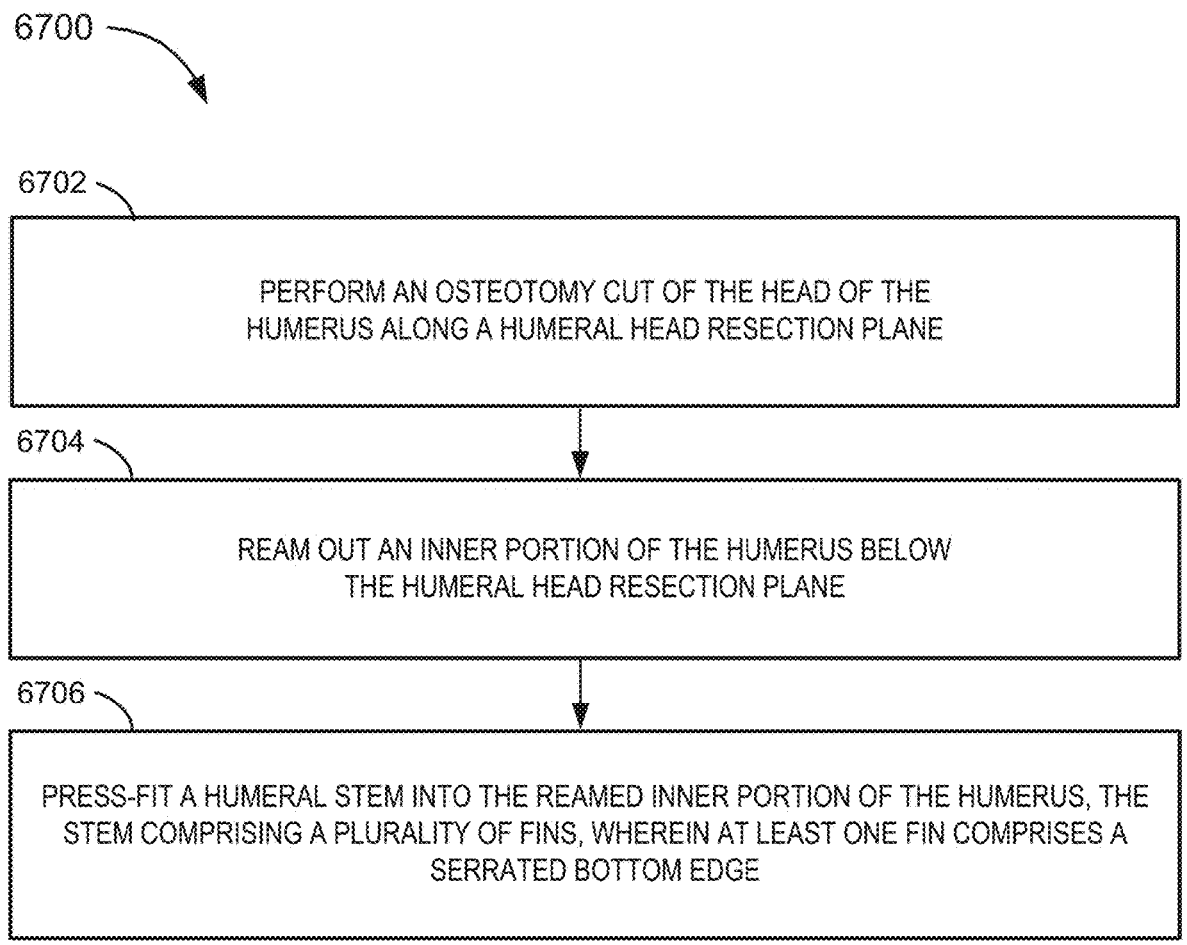
FIG. 67 illustrates a flowchart related to a method of implanting a humeral implant in a humerus of a patient, in accordance with some example embodiments.

FIG. 67 illustrates a flowchart 6700 for an example method of implanting a humeral implant in a humerus of a patient, as described anywhere in this disclosure. Although particular steps are described herein, the present application is not so limited and alternative methods may include a subset of these steps, in the same or different order, and may additionally include one or more addition steps not described herein.

Step 6702 includes performing an osteotomy cut of the head of the humerus along a humeral head resection plane. For example, such an osteotomy may be performed as previously described in connection with at least FIGS. 1-4.

Step 6704 includes reaming out an inner portion of the humerus below the humeral head resection plane. For example, such reaming may be performed as previously described in connection with at least FIGS. 13-15.

Step 6706 includes press-fitting a humeral stem into the reamed inner portion of the humerus, the stem comprising a plurality of fins, wherein at least one fin comprises a serrated bottom edge. For example, such press-fitting of humeral stem 5300 may be carried out as previously described in connection with at least any of FIGS. 43-46 and 53-61.

Example Methods of Manufacture

The disclosure now turns to one or more example methods of manufacturing a humeral implant, as described anywhere in this disclosure.

Figure 68:
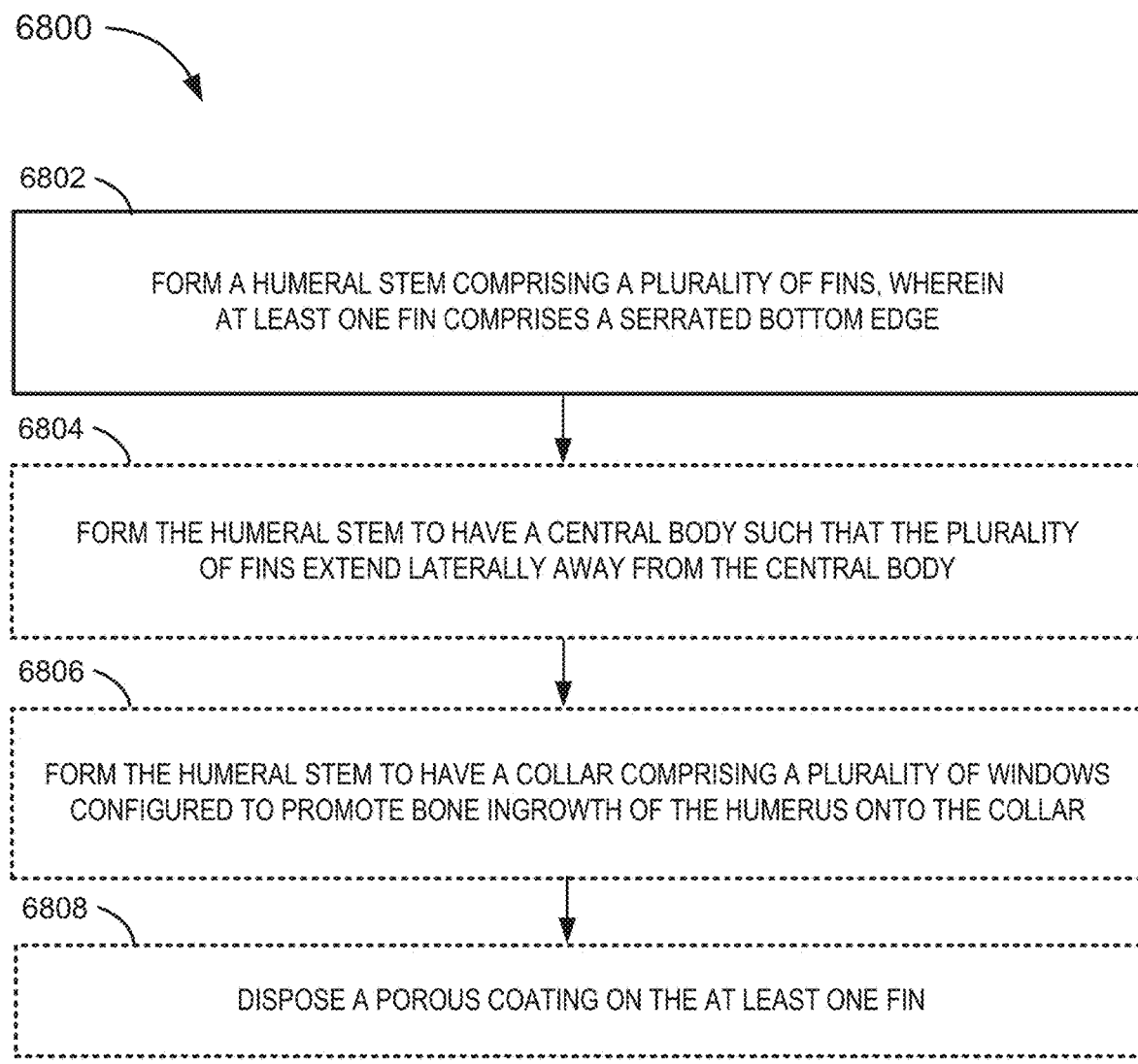
FIG. 68 illustrates a flowchart related to a method of manufacturing a humeral implant, in accordance with some example embodiments.

FIG. 68 illustrates a flowchart 600 for an example method of manufacturing such a humeral implant. Although particular steps are described herein, the present application is not so limited and alternative methods may include a subset of these steps, in the same or different order, and may additionally include one or more addition steps not described herein.

Step 6802 includes forming a humeral stem comprising a plurality of fins, wherein at least one fin comprises a serrated bottom edge. For example, humeral stem 5300 can be formed substantially as described in connection with any of FIGS. 53-61.

In some embodiments, a step 6804 may include forming the humeral stem to have a central body such that the plurality of fins extend radially away from the central body. For example, humeral stem 5300 can be formed to have central body 5340 substantially as described in connection with any of FIGS. 53-61.

In some embodiments, a step 6806 may include forming the humeral stem to have a collar comprising a plurality of windows. For example, humeral stem 5300 can be formed to have collar 5310 substantially as described in connection with any of FIGS. 53-61.

In some embodiments, a step 6808 may include disposing a porous coating on the at least one fin and the collar. For example, porous coating 5360 can be applied to any portions of humeral stem 5300 substantially as described in connection with any of FIGS. 53-61.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The invention claimed is:

1. A surgical kit for shoulder arthroplasty, the surgical kit comprising a plurality of humeral implants, wherein each of the plurality of humeral implants comprises a collar, a central body extending distally from and originating at the collar, and a plurality of fins extending downward and radially outward from the central body and having a proximal portion connected to and originating at the central body, wherein at least some of the plurality of humeral implants have a collar of a same size and a central body of a same size, and wherein the at least some of the plurality of humeral implants having collars and central bodies of the same size have a plurality of fins of a different size, and wherein, on a largest size humeral implant of the at least some of the plurality of humeral implants, the plurality of fins protrude radially relatively farther from a centerline of the largest size humeral implant compared to smaller size humeral implants of the at least some of the plurality of humeral implants.

2. The kit of claim 1, wherein each of the plurality of fins comprises a serrated bottom edge, and wherein on the largest size humeral implant, the plurality of fins comprise relatively more serrated points compared to smaller size humeral implants.

3. The kit of claim 1, further comprising a centering guide configured to fit on a humeral osteotomy surface.

4. The kit of claim 3, wherein the centering guide comprises a base with a size equal to the size of the collars of the at least some of the plurality of humeral implants.

5. The kit of claim 4, wherein the centering guide comprises at least a first marking corresponding to a radial position of a plurality of fins of a smallest size humeral implant of the at least some of the plurality of humeral implants.

6. The kit of claim 1, comprising a collar reamer for forming a recess in a humeral osteotomy surface.

7. The kit of claim 1, further comprising a plurality of humeral punches having sizes corresponding to the radial protrusion of fins of different sizes of the plurality of humeral implants.

8. The kit of claim 7, further comprising a plurality of covers of different sizes configured to cover portions of humeral osteotomies prepared with different ones of the plurality of humeral punches.

9. The kit of claim 1, further comprising at least one humeral head configured to couple to at least one of the plurality of humeral implants.

10. The kit of claim 9, further comprising at least one neck implant configured to couple to the at least one humeral head and at least one of the plurality of humeral implants.

11. The kit of claim 1, wherein at least one fin of the plurality of fins on at least one of the plurality of humeral implants has a distal portion that extends farther distally than a bottom surface of the central body, wherein the distal portion of the at least one fin of the plurality of fins comprises:
an inner bottom edge originating at and extending downward from the bottom surface of the central body, wherein a radial distance between the inner bottom edge of the at least one fin and a central axis of the humeral implant increases along a distal length of extension of the at least one fin; and
a serrated outer bottom edge originating at and extending downward from a side edge of the proximal portion of the at least one fin, wherein a radial distance between the serrated outer bottom edge of the at least one fin and the central axis of the humeral implant decreases along a distal length of extension of the at least one fin until meeting the inner bottom edge at a lowermost tip of the at least one fin.

12. The kit of claim 11, wherein the inner bottom edge and the serrated outer bottom edge of the at least one fin continually approach each other all the way from the bottom surface of the central body to a distal location of the lowermost tip of the at least one fin.

13. The kit of claim 11, wherein at least the serrated outer bottom edge of the at least one fin is configured to cut into and compact bone of the metaphysis of a humerus toward relatively denser cancellous bone of a peripheral portion of the humerus when press-fit therein.

14. The kit of claim 1, wherein the central body of at least one of the plurality of humeral implants has a substantially cylindrical shape that tapers along its length of extension.

15. The kit of claim 1, wherein the collar of at least one of the plurality of humeral implants comprises an outer ring, a central portion, and plurality of windows formed by portions of the collar coupling the outer ring and the central portion.

16. The kit of claim 15, wherein the collar has a substantially circular shape.

17. A surgical kit for shoulder arthroplasty, the surgical kit comprising:
a plurality of humeral implants, wherein each of the plurality of humeral implants comprises:
a collar;
a central body extending distally from and originating at the collar; and
a plurality of fins extending downward and radially outward from the central body and having a proximal portion connected to and originating at the central body;
wherein at least some of the plurality of humeral implants have a collar of a same size and a central body of a same size, and wherein the at least some of the plurality of humeral implants having collars and central bodies of the same size have a plurality of fins of a different size, and wherein, on a largest size humeral implant of the at least some of the plurality of humeral implants, the plurality of fins protrude radially relatively farther from a centerline of the largest size humeral implant compared to smaller size humeral implants of the at least some of the plurality of humeral implants;

a centering guide having a size the same as the collars of the at least some of the plurality of humeral implants; and a reamer having a size the same as the collars of the at least some of the plurality of humeral implants.

18. The kit of claim 17, further comprising a plurality of humeral punches having different sizes corresponding to a radial extent of the fins of different sizes of the at least some of the plurality of humeral implants.

* * * * *